US012133981B2

(12) United States Patent
Lee et al.

(10) Patent No.: US 12,133,981 B2
(45) Date of Patent: Nov. 5, 2024

(54) NEUROSTIMULATION WAVEFORMS HAVING A BASE COMPONENT AND A HIGH FREQUENCY COMPONENT, AND ASSOCIATED SYSTEMS AND METHODS

(71) Applicant: Nevro Corp., Redwood City, CA (US)

(72) Inventors: Dongchul Lee, Agua Dulce, CA (US); Kerry Bradley, Glendale, CA (US)

(73) Assignee: Nevro Corp., Redwood City, CA (US)

( * ) Notice: Subject to any disclaimer, the term of this patent is extended or adjusted under 35 U.S.C. 154(b) by 67 days.

(21) Appl. No.: 17/837,726

(22) Filed: Jun. 10, 2022

(65) Prior Publication Data

US 2022/0401730 A1 Dec. 22, 2022

Related U.S. Application Data

(60) Provisional application No. 63/209,628, filed on Jun. 11, 2021.

(51) Int. Cl.
*A61N 1/36* (2006.01)
*A61N 1/05* (2006.01)

(52) U.S. Cl.
CPC ....... *A61N 1/36071* (2013.01); *A61N 1/0551* (2013.01); *A61N 1/36062* (2017.08); *A61N 1/36171* (2013.01); *A61N 1/36175* (2013.01)

(58) Field of Classification Search
CPC ......................... A61N 1/36071; A61N 1/36062
USPC .......................................................... 607/59
See application file for complete search history.

(56) References Cited

U.S. PATENT DOCUMENTS

| | | | |
|---|---|---|---|
| 8,340,775 B1 * | 12/2012 | Cullen | A61N 1/37247 607/46 |
| 8,355,797 B2 | 1/2013 | Carparso | |
| 8,649,874 B2 | 2/2014 | Alataris | |
| 9,327,121 B2 | 5/2016 | Thacker et al. | |
| 10,537,740 B2 | 1/2020 | Cabunaru | |
| 10,682,516 B1 | 6/2020 | Thacker et al. | |
| 11,235,153 B2 | 2/2022 | Kibler et al. | |
| 2006/0229687 A1 * | 10/2006 | Goetz | A61N 1/36185 607/66 |
| 2011/0071593 A1 | 3/2011 | Parker | |

(Continued)

FOREIGN PATENT DOCUMENTS

| WO | WO-2015179177 | 11/2015 |
|---|---|---|
| WO | WO-2019191601 | 10/2019 |

(Continued)

OTHER PUBLICATIONS

Kim et al. "Introduction of Clinical Electro-Analgesia Therapy," Dept of Physcial Therapy, Pohang St. Mary's Hospital—vol. 3, No. 4, 1996, 7 pages.

(Continued)

*Primary Examiner* — Nadia A Mahmood
(74) *Attorney, Agent, or Firm* — Perkins Coie LLP

(57) ABSTRACT

The present technology provides systems and methods for directly suppressing nerve cells by delivering electrical stimulation having relatively long pulse widths and at amplitudes below an activation threshold of the nerve cells. For example, some embodiments include delivering a therapy signal having individual pulses with pulse widths of between about 5 ms and 100 ms. Directly suppressing the nerve cells is expected to reduce the transmission of pain signals.

33 Claims, 14 Drawing Sheets

(56) References Cited

U.S. PATENT DOCUMENTS

| | | |
|---|---|---|
| 2013/0289661 A1 | 10/2013 | Griffith et al. |
| 2014/0071349 A1 | 3/2014 | Ramo et al. |
| 2014/0277281 A1 | 9/2014 | Grandhe et al. |
| 2014/0277288 A1 | 9/2014 | Archer |
| 2016/0074664 A1 | 3/2016 | De Ridder |
| 2016/0121126 A1 | 5/2016 | Marnfeldt et al. |
| 2016/0129272 A1 | 5/2016 | Hou et al. |
| 2018/0056073 A1 | 3/2018 | Torgerson |
| 2018/0154144 A1 | 6/2018 | Brink et al. |
| 2018/0256892 A1 | 9/2018 | Wong |
| 2018/0369593 A1 | 12/2018 | Johanek |
| 2019/0001139 A1 | 1/2019 | Mishra et al. |
| 2020/0061380 A1 | 2/2020 | Zhang et al. |
| 2020/0094055 A1 | 3/2020 | Manogue |
| 2020/0171309 A1 | 6/2020 | Alataris |
| 2020/0406041 A1 | 12/2020 | Cao |
| 2021/0228881 A1 | 7/2021 | Bradley |
| 2021/0379386 A1 | 12/2021 | Parker et al. |
| 2022/0062636 A1 | 3/2022 | Vallejo et al. |

FOREIGN PATENT DOCUMENTS

| | | |
|---|---|---|
| WO | WO-2020236946 | 11/2020 |
| WO | WO-2021080727 | 4/2021 |

OTHER PUBLICATIONS

Gilligan et al., "An Implantable restorative-neurostimulator for refactory mechanical chronic low back pain: a randomized sham-controlled clinical trial," PAIN, 2021 13 pages.

International Search Report and Written Opinion for International Patent Application No. PCT/US22/33039, Applicant: Nevro Corp., mailed Sep. 30, 2022, 10 pages.

Jones et al., "Neuromodulation using ultra low frequency current waveform reversibly blocks axonal conduction and chronic pain," Science Translational Medicine, Aug. 2021, 13 pages.

Sun et al., "Closed-Loop Neurostimulation: The Clinical Experience," Neurotherapeautics, 2014, 11 pages.

* cited by examiner

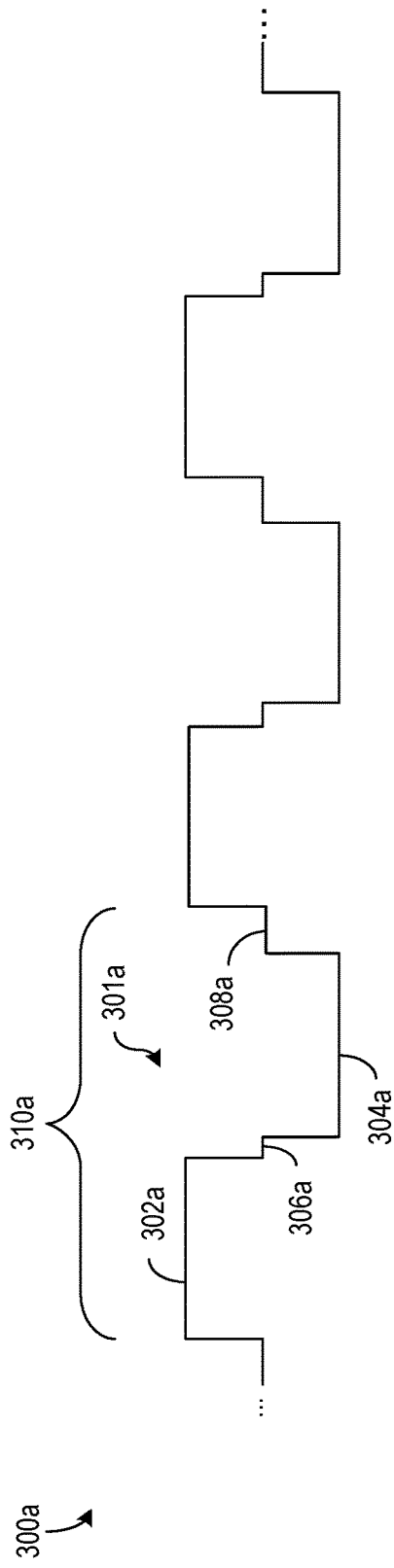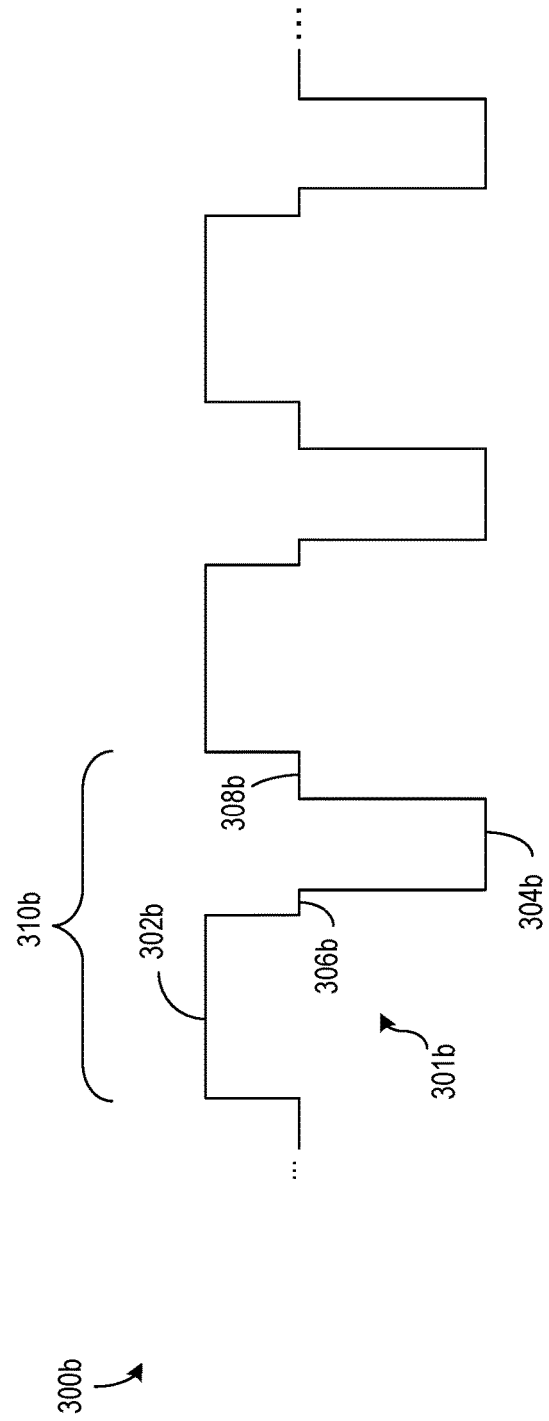
FIG. 3A
FIG. 3B

NEUROSTIMULATION WAVEFORMS HAVING A BASE COMPONENT AND A HIGH FREQUENCY COMPONENT, AND ASSOCIATED SYSTEMS AND METHODS

CROSS-REFERENCE TO RELATED APPLICATION(S)

The present application claims priority to U.S. Provisional Application No. 63/209,628, filed Jun. 11, 2021, the disclosure of which is incorporated by reference herein in its entirety.

TECHNICAL FIELD

The present technology is directed towards spinal cord modulation for inhibiting pain, and associated systems and methods.

BACKGROUND

Neurological stimulators have been developed to treat pain, movement disorders, functional disorders, spasticity, cancer, cardiac disorders, and various other medical conditions. Implantable neurological stimulation systems generally have an implantable pulse generator and one or more leads that deliver electrical pulses to neurological tissue or muscle tissue. For example, several neurological stimulation systems for spinal cord stimulation ("SCS") have cylindrical leads that include a lead body with a circular cross-sectional shape and one or more conductive rings spaced apart from each other at the distal end of the lead body. The conductive rings operate as individual electrodes and, in many cases, the SCS leads are implanted percutaneously through a needle inserted into the epidural space, with or without the assistance of a stylet.

Once implanted, the pulse generator applies electrical pulses to the electrodes, which in turn modify the function of the patient's nervous system, such as by altering the patient's responsiveness to sensory stimuli and/or altering the patient's motor-circuit output. In pain treatment, the pulse generator applies electrical pulses to the electrodes, which in turn can generate sensations that mask or otherwise alter the patient's sensation of pain. For example, in many cases, patients report a tingling or paresthesia that is perceived as more pleasant and/or less uncomfortable than the underlying pain sensation. While this may be the case for many patients, many other patients may report less beneficial effects and/or results. Accordingly, there remains a need for improved techniques and systems for addressing patient pain.

BRIEF DESCRIPTION OF THE DRAWINGS

FIGS. 3A-3H illustrate representative wave forms associated with therapy signals applied to patients in accordance with particular embodiments of the present technology.

DETAILED DESCRIPTION

Figure 1A:
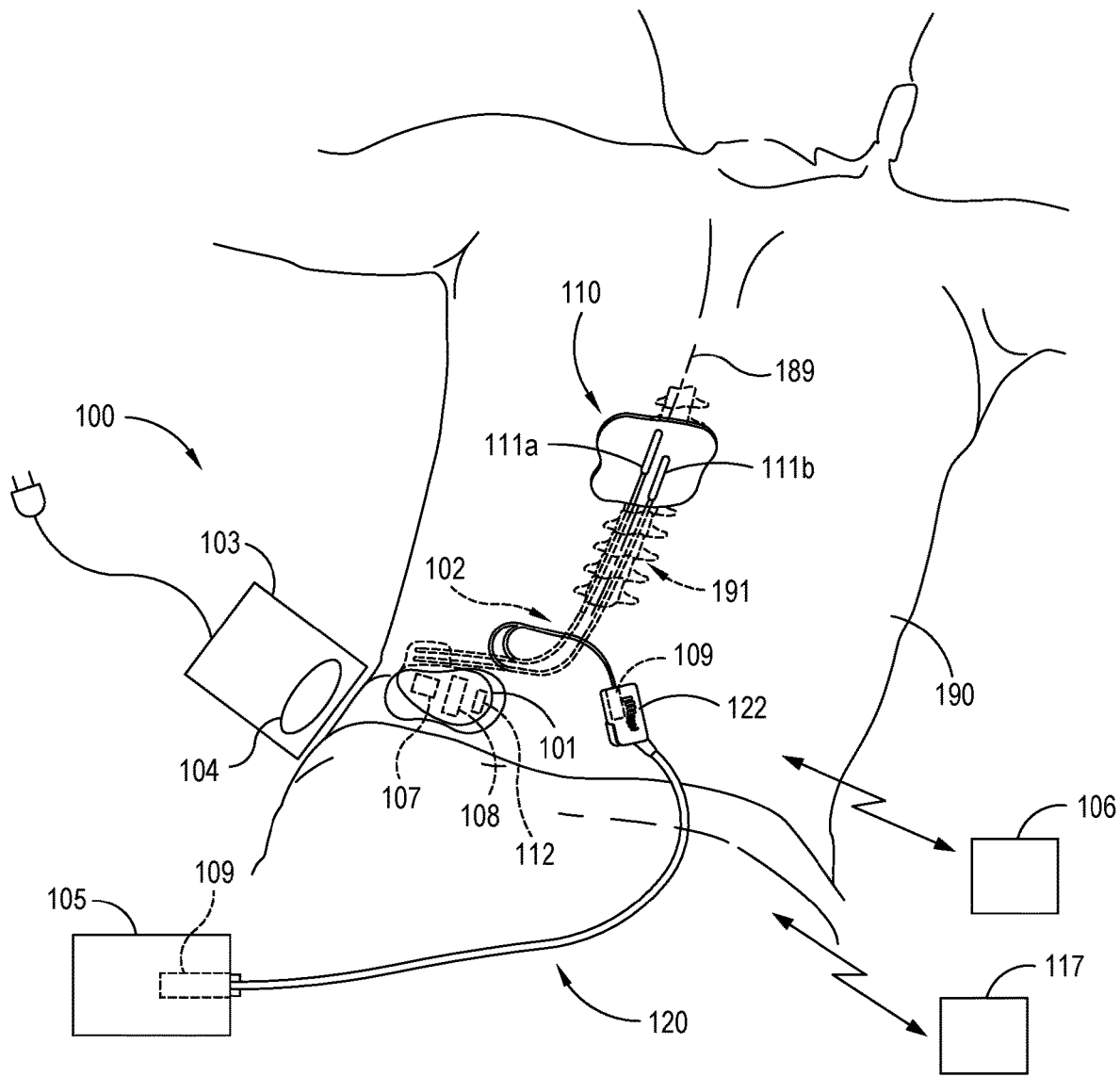
FIG. 1A is a partially schematic illustration of an implantable spinal cord modulation system positioned at a patient's spine to deliver therapeutic signals in accordance with some embodiments of the present technology.

The present technology is generally directed to neurostimulation for the treatment of pain. In some embodiments, the present technology provides therapy signals having relatively long pulse widths, such as between about 5 ms and about 2 seconds. In some embodiments, the therapy signals further include offset high frequency pulses and/or bursts of high frequency pulses occurring during the relatively long pulse widths. For example, the therapy signal can have a base component having a non-zero amplitude and a pulse width in a pulse width range of from about 5 ms and about 2 second, and a high frequency component including high frequency pulses having a frequency in a frequency range of from about 1.2 kHz to about 100 kHz and occurring from the non-zero amplitude of the base component. Without being bound by theory, therapy signals in accordance with the present technology are expected to advantageously address one or more physiologic factors contributing to patient pain, such as by directly and/or indirectly suppressing neurons that transmit pain signals to a patient's pain perception centers.

Definitions of selected terms are provided under Heading 1.0 ("Definitions"). General aspects of the present technology are described below under Heading 2.0 ("Overview of Present Technology"). Representative treatment systems and their characteristics are described under Heading 3.0 ("System Characteristics") with reference to FIGS. 1A, 1B and 2. Representative methods for treating patients are described under Heading 4.0 ("Representative Signals for Directly Suppressing Cells") with reference to FIGS. 3A-4. Representative results from animal studies are described under Heading 5.0 ("Representative Results from Animal Studies") with reference to FIGS. 5-6B. Representative examples are described under Heading 6.0 ("Representative Examples"). The headings provided herein are for convenience only and do not interpret the scope or meaning of the claimed present technology.

1.0 Definitions

Unless otherwise stated, the terms "generally," "about," and "approximately" refer to values within 10% of a stated value. For example, the use of the term "about 100" refers to a range of 90 to 110, inclusive. In instances where relative terminology is used in reference to something that does not include a numerical value, the terms are given their ordinary meaning to one skilled in the art.

As used herein, and unless otherwise noted, the terms "modulate," "modulation," "stimulate," and "stimulation" refer generally to signals that have an inhibitory, excitatory, and/or other effect on a target neural population. Accordingly, a spinal cord "stimulator" can have an inhibitory effect on certain neural populations. Moreover, the use of the terms "suppress" and "inhibit" in relation to a therapy signal's effect on a neuron refers to a reduction in the neuron's firing rate relative to the neuron's baseline firing rate in the absence of the therapy signal, and does not necessarily refer to a complete elimination of action potentials in the neuron.

As used herein, "proximate a spinal cord region" refers to the placement of a signal delivery element such that it can deliver electrical stimulation to a neural population associated with the spinal cord or associated nervous system structures. For example, "proximate a spinal cord region" includes, but is not limited to, the relative lead positions described and shown in FIG. 1B, as well as other positions not expressly described herein.

As used herein, the term "pulse width" refers to the width of any phase of a repeating pulse, such as the portion of a pulse at a given polarity, unless explicitly described otherwise. For example, the use of the term pulse width with respect to a signal having bi-phasic pulses can refer to the duration of an anodic pulse phase or a cathodic pulse phase. The use of the term pulse width with respect to a signal having monophasic pulses can refer to the duration of the monophasic pulse phase.

2.0 Overview of the Present Technology

The present technology is directed generally to spinal cord modulation and associated systems and methods for treating pain. In some embodiments, representative techniques include applying a therapy signal having a relatively long pulse width of about 5 ms to about 2 seconds to a spinal cord region of a patient. In some embodiments, the therapy signals further include offset high frequency pulses and/or bursts of high frequency pulses occurring during the relatively long pulse widths. The therapy signal can be applied at an amplitude that is below the activation threshold of neurons adjacent the signal delivery element. Without being bound by theory, the use of therapy signals in accordance with the present technology is expected to advantageously address one or more physiologic factors contributing to patient pain, such as by directly and/or indirectly suppressing neurons that transmit pain signals to a patient's pain perception centers. Therapy signals applied in accordance with the present technology are expected to reduce various types of pain, including but not limited to chronic low back pain (e.g., neuropathic pain, and/or nociceptive pain, and/or other types of pain, depending upon the patient) and/or chronic leg pain.

The present technology represents a departure from conventional SCS. Conventional SCS systems were originally derived from the gate control theory of pain, which suggested that the activity of large diameter sensory fiber systems could influence small diameter pain fiber transmission to the higher neural centers where the pain signals result in the conscious perception of pain. The interaction between the large diameter and small diameter neurons was thought to be mediated by inhibitory interneurons in the dorsal horn. Exciting these inhibitory interneurons was thought to have a suppressing influence on 'wide dynamic range' (WDR) neurons, which are considered the main output for pain of the spinal gate. The early clinical targets for stimulation included the dorsal columns, which are the central primary afferent pathway for innocuous sensations from large sensory fibers. This "conventional" stimulation required the patient experience paresthesia, but resulted in reasonable pain relief for a large number of patients over decades.

During the last two decades, mechanistic studies began to highlight the idea that SCS was not stopping small fiber transmission (the 'drive' behind nociceptive pain), but rather was treating central sensitization. Central sensitization is the amplification of pain circuits, for example, in the dorsal horn. In particular, central sensitization can manifest as (1) an increase in sensitivity of WDR neurons to afferent input (resulting in hyperalgesia, allodynia, etc.); (2) activity of the WDR neurons in the absence of afferent input (resulting in spontaneous, ongoing pain); and/or (3) concomitant hypersensitization of nominal 'nociceptive-specific' (NS) projection neurons (also resulting in hyperalgesia). It is believed that paresthesia-based SCS inhibited spontaneous WDR neuron activity very indirectly. Stimulating the dorsal columns would provide an epiphenomenon of paresthesia, but would also send signals into the spinal gate. These signals entering the gate would drive the inhibitory interneurons, which then could inhibit the WDR neurons. To achieve inhibition of the WDR neurons, both (i) the correct dorsal column fibers had to be stimulated and (ii) the inhibitory interneurons had to provide the key link between the dorsal column fibers and the hyperactive WDR neurons. If the correct dorsal column fibers could not be activated (for example, if they were too deep in the spinal cord, if the lead position was not optimal, etc.), or if the inhibitory interneurons were not adequate for the task (e.g., if there were too few inhibitory interneurons to inhibit the WDR neurons), pain relief could not be achieved.

High Frequency SCS (e.g., stimulation at a frequency greater than about 1.2 kHz) allowed for superior pain relief in more patients than conventional stimulation, particularly in patients with neuropathic back pain. Mechanistic studies of high frequency SCS, in general agreement with clinical data, have shown that the inhibitory interneurons can be directly driven by the stimulation field, without the need to activate dorsal column fibers. Additionally, mechanistic studies of 10 kHz low-intensity SCS have shown that both WDR and NS neurons can be inhibited. Because it is believed that high frequency SCS may bypass the step of activating the dorsal columns, high frequency SCS may enable a greater degree of flexibility for lead placement and does not require that the patient experience paresthesia. Indeed, the clinically-effective stimulation amplitudes of 10 kHz SCS are below the dorsal column threshold.

The present technology, however, includes signals that are expected to directly suppress target neurons in the superficial dorsal horn pain circuits (e.g., the NS and WDR neurons) in lieu of and/or in addition to suppressing neurons via other mechanisms. For example, as described in greater detail below, signals having a pulse width between about 5 ms and about 2 seconds can electrically mediate the function of the target neurons to directly suppress the target neurons. Without intending to be bound by theory, the signals having a pulse width between about 5 ms and about 2 seconds may cause neural membrane channels of the target neurons to enter a net inactivate state that prevents the neurons from firing. This is in contrast to conventional SCS and high frequency SCS, both of which indirectly mediate the NS and/or WDR neurons by inducing release of neurotransmitter from an upstream neuron (e.g., dorsal column fibers and/or inhibitory interneurons), that may have an inhibitory effect on the downstream target neuron. Without being bound by theory, it is expected that directly targeting the NS and WDR neurons bypasses the need to activate the inhibitory interneurons to achieve a reduction in pain transmission. Accordingly, the present technology provides therapy signals and associated systems and methods that directly suppress at least a subset of target neurons, such as NS and WDR neurons, to provide pain relief. The present technology further provides therapy signals that incorporate both a high frequency component and a base component having a pulse width between about 5 ms and about 2 seconds such that the signal may address pain through multiple mechanisms of action and/or a combination of the previously described mechanisms of action (e.g., direct suppression as a result of the base component and inhibitory interneuron activation by the high frequency component). As demonstrated below, this combination may provide superior pain relief relative to existing therapy signals in at least some patients.

Specific details of certain embodiments of the disclosure are described below with reference to methods for modulating one or more target neural populations (e.g., nerves) or sites of a patient, and associated implantable structures for providing the modulation. Although selected embodiments are described below with reference to modulating the dorsal column, dorsal horn, dorsal root, dorsal root entry zone, and/or other particular regions of the spinal column to control pain, the modulation may in some instances be directed to other neurological structures and/or target neural populations of the spinal cord and/or other neurological tissues. Some embodiments can have configurations, components or procedures different than those described in this section, and other embodiments may eliminate particular components or procedures. A person of ordinary skill in the relevant art, therefore, will understand that the present disclosure may include other embodiments with additional elements, and/or may include other embodiments without several of the features shown and described below with reference to FIGS. 1A-4.

3.0 System Characteristics

FIG. 1A schematically illustrates a representative patient therapy system 100 for treating a patient's motor and/or other functioning, arranged relative to the general anatomy of the patient's spinal column 191. The system 100 can include a signal generator 101 (e.g., an implanted or implantable pulse generator or IPG), which may be implanted subcutaneously within a patient 190 and coupled to one or more signal delivery elements or devices 110. The signal delivery elements or devices 110 may be implanted within the patient 190, at or off the patient's spinal cord midline 189. The signal delivery elements 110 carry features for delivering therapy to the patient 190 after implantation. The signal generator 101 can be connected directly to the signal delivery devices 110, or it can be coupled to the signal delivery devices 110 via a signal link, e.g., a lead extension 102. In some embodiments, the signal delivery devices 110 can include one or more elongated lead(s) or lead body or bodies 111 (identified individually as a first lead 111a and a second lead 111b). As used herein, the terms signal delivery device, signal delivery element, lead, and/or lead body include any of a number of suitable substrates and/or supporting members that carry electrodes/devices for providing therapy signals to the patient 190. For example, the lead or leads 111 can include one or more electrodes or electrical contacts that direct electrical signals into the patient's tissue, e.g., to provide for therapeutic relief. In some embodiments, the signal delivery elements 110 can include structures other than a lead body (e.g., a paddle) that also direct electrical signals and/or other types of signals to the patient 190, e.g., as disclosed in U.S. Patent Application Publication No. 2018/0256892, incorporated herein by reference in its entirety. For example, paddles may be more suitable for patients with spinal cord injuries that result in scarring or other tissue damage that impedes cylindrical leads.

In some embodiments, one signal delivery device may be implanted on one side of the spinal cord midline 189, and a second signal delivery device may be implanted on the other side of the spinal cord midline 189. For example, the first and second leads 111a, 111b shown in FIG. 1A may be positioned just off the spinal cord midline 189 (e.g., about 1 mm offset) in opposing lateral directions so that the two leads 111a, 111b are spaced apart from each other by about 2 mm. In some embodiments, the leads 111 may be implanted at a vertebral level ranging from, for example, about T4 to about T12. In some embodiments, one or more signal delivery devices can be implanted at other vertebral levels, e.g., as disclosed in U.S. Pat. No. 9,327,121, incorporated herein by reference in its entirety.

The signal generator 101 can transmit signals (e.g., electrical signals) to the signal delivery elements 110 that excite and/or suppress target nerves. The signal generator 101 can include a machine-readable (e.g., computer-readable or controller-readable) medium containing instructions for generating and transmitting suitable therapy signals, such as those described below with respect to FIGS. 3A-3D. The signal generator 101 and/or other elements of the system 100 can include one or more processor(s) 107, memory unit(s) 108, and/or input/output device(s) 112. Accordingly, the process of providing modulation signals, providing guidance information for positioning the signal delivery devices 110, establishing battery charging and/or discharging parameters, and/or executing other associated functions can be performed by computer-executable instructions contained by, on, or in computer-readable media located at the pulse generator 101 and/or other system components. Further, the pulse generator 101 and/or other system components may include dedicated hardware, firmware, and/or software for executing computer-executable instructions that, when executed, perform any one or more methods, processes, and/or sub-processes described in the materials incorporated herein by reference. The dedicated hardware, firmware, and/or software also serve as "means for" performing the methods, processes, and/or sub-processes described herein. The signal generator 101 can also include multiple portions, elements, and/or subsystems (e.g., for directing signals in accordance with multiple signal delivery parameters), carried in a single housing, as shown in FIG. 1A, or in multiple housings. For example, the signal generator can include some components that are implanted (e.g., a circuit that directs signals to the signal delivery device 110), and some that are not (e.g., a power source). The computer-executable instructions can be contained on one or more media that are implanted within the patient and/or positioned external to the patient, depending on the embodiment.

The signal generator 101 can also receive and respond to an input signal received from one or more sources. The input signals can direct or influence the manner in which the therapy, charging, and/or process instructions are selected, executed, updated, and/or otherwise performed. The input signals can be received from one or more sensors (e.g., an input device 112 shown schematically in FIG. 1A for purposes of illustration) that are carried by the signal generator 101 and/or distributed outside the signal generator 101 (e.g., at other patient locations) while still communicating with the signal generator 101. The sensors and/or other input devices 112 can provide inputs that depend on or reflect patient state (e.g., patient position, patient posture, and/or patient activity level), and/or inputs that are patient-independent (e.g., time). Still further details are included in U.S. Pat. No. 8,355,797, incorporated herein by reference in its entirety.

In some embodiments, the signal generator 101 and/or signal delivery devices 110 can obtain power to generate the therapy signals from an external power source 103. For example, the external power source 103 can by-pass an implanted signal generator and generate a therapy signal directly at the signal delivery devices 110 (or via signal relay components). The external power source 103 can transmit power to the implanted signal generator 101 and/or directly to the signal delivery devices 110 using electromagnetic induction (e.g., RF signals). For example, the external power source 103 can include an external coil 104 that communicates with a corresponding internal coil (not shown) within the implantable signal generator 101, signal delivery devices 110, and/or a power relay component (not shown). The external power source 103 can be portable for ease of use.

In some embodiments, the signal generator 101 can obtain the power to generate therapy signals from an internal power source, in addition to or in lieu of the external power source 103. For example, the implanted signal generator 101 can include a non-rechargeable battery or a rechargeable battery to provide such power. When the internal power source includes a rechargeable battery, the external power source 103 can be used to recharge the battery. The external power source 103 can in turn be recharged from a suitable power source (e.g., conventional wall power).

During at least some procedures, an external stimulator or trial modulator 105 can be coupled to the signal delivery elements 110 during an initial procedure, prior to implanting the signal generator 101. For example, a practitioner (e.g., a physician and/or a company representative) can use the trial modulator 105 to vary the modulation parameters provided to the signal delivery elements 110 in real time, and select optimal or particularly efficacious parameters. These parameters can include the location from which the electrical signals are emitted, as well as the characteristics of the electrical signals provided to the signal delivery devices 110. In some embodiments, input is collected via the external stimulator or trial modulator 105 and can be used by the clinician to help determine what parameters to vary. In a typical process, the practitioner uses a cable assembly 120 to temporarily connect the trial modulator 105 to the signal delivery device 110. The practitioner can test the efficacy of the signal delivery devices 110 in an initial position. The practitioner can then disconnect the cable assembly 120 (e.g., at a connector 122), reposition the signal delivery devices 110, and reapply the electrical signals. This process can be performed iteratively until the practitioner obtains the desired position for the signal delivery devices 110. Optionally, the practitioner may move the partially implanted signal delivery devices 110 without disconnecting the cable assembly 120. Furthermore, in some embodiments, the iterative process of repositioning the signal delivery devices 110 and/or varying the therapy parameters may not be performed.

The signal generator 101, the lead extension 102, the trial modulator 105 and/or the connector 122 can each include a receiving element 109. Accordingly, the receiving elements 109 can be patient implantable elements, or the receiving elements 109 can be integral with an external patient treatment element, device or component (e.g., the trial modulator 105 and/or the connector 122). The receiving elements 109 can be configured to facilitate a simple coupling and decoupling procedure between the signal delivery devices 110, the lead extension 102, the pulse generator 101, the trial modulator 105 and/or the connector 122. The receiving elements 109 can be at least generally similar in structure and function to those described in U.S. Patent Application Publication No. 2011/0071593, incorporated by reference herein in its entirety.

After the signal delivery elements 110 are implanted, the patient 190 can receive therapy via signals generated by the trial modulator 105, generally for a limited period of time. During this time, the patient wears the cable assembly 120 and the trial modulator 105 outside the body. Assuming the trial therapy is effective or shows the promise of being effective, the practitioner then replaces the trial modulator 105 with the implanted signal generator 101, and programs the signal generator 101 with therapy programs selected based on the experience gained during the trial period. Optionally, the practitioner can also replace the signal delivery elements 110. In still further embodiments, the signal generator 101 can be implanted without first undergoing a trial period. Once the implantable signal generator 101 has been positioned within the patient 190, the therapy programs provided by the signal generator 101 can still be updated remotely via a wireless physician's programmer 117 (e.g., a physician's laptop, a physician's remote or remote device, etc.) and/or a wireless patient programmer 106 (e.g., a patient's laptop, patient's remote or remote device, etc.). Generally, the patient 190 has control over fewer parameters than does the practitioner. For example, the capability of the patient programmer 106 may be limited to starting and/or stopping the signal generator 101, and/or adjusting the signal amplitude within a present amplitude range. The patient programmer 106 may be configured to accept inputs corresponding to pain relief, motor functioning and/or other variables, such as medication use. Accordingly, more generally, embodiments of the present technology include receiving patient feedback, via a sensor, that is indicative of, or otherwise corresponds to, the patient's response to the signal. Feedback includes, but is not limited to, motor, sensory, and verbal feedback. In response to the patient feedback, one or more signal parameters can be adjusted, such as frequency, pulse width, amplitude, or delivery location.

Figure 1B:
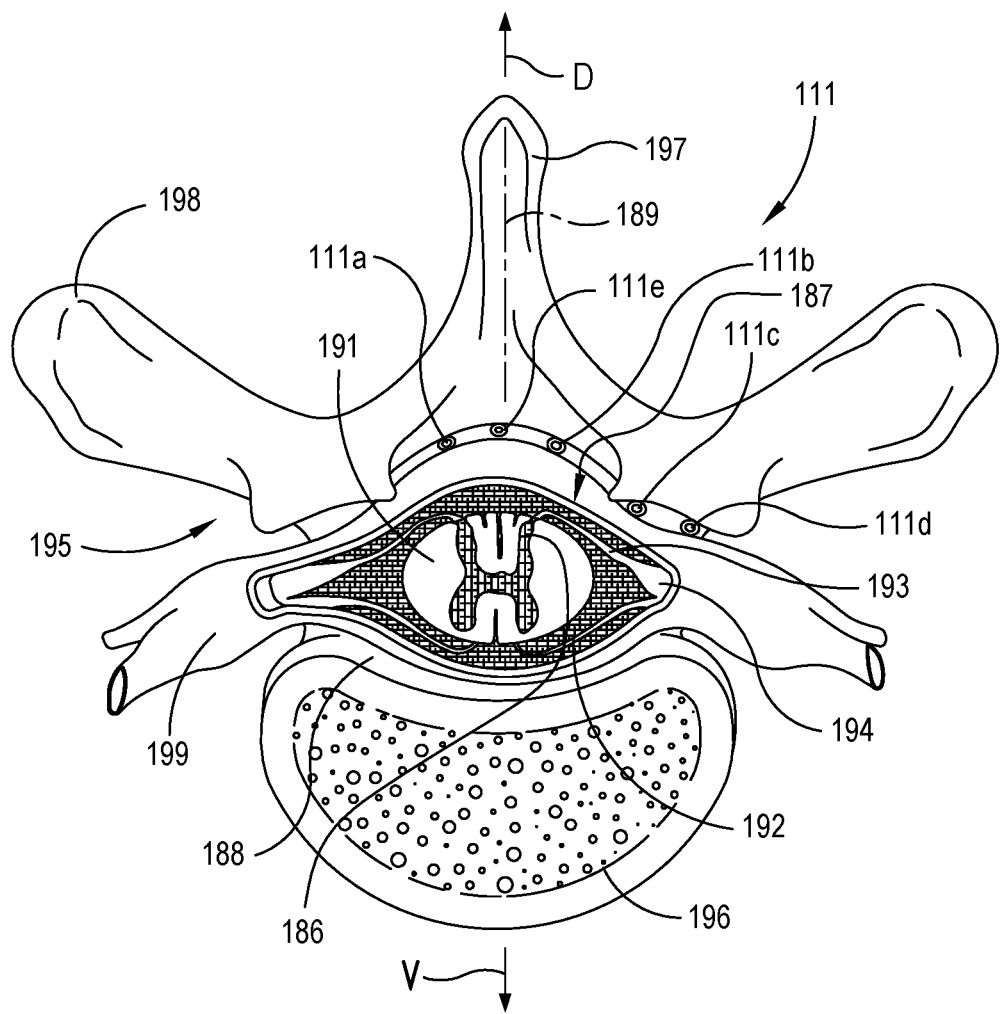
FIG. 1B is a partially schematic, cross-sectional illustration of a patient's spine, illustrating representative locations for implanted lead bodies in accordance with some embodiments of the present technology.

FIG. 1B is a cross-sectional illustration of the spinal cord 191 and an adjacent vertebra 195 (based generally on information from Crossman and Neary, "Neuroanatomy," 1995 (published by Churchill Livingstone)), along with multiple leads 111 (shown as leads 111a-111e) implanted at representative locations. For purposes of illustration, multiple leads 111 are shown in FIG. 1B implanted in a single patient. In addition, for purposes of illustration, the leads 111 are shown as elongated leads however, leads 111 can be paddle leads. In actual use, any given patient will likely receive fewer than all the leads 111 shown in FIG. 1B.

The spinal cord 191 is situated within a vertebral foramen 188, between a ventrally located ventral body 196 and a dorsally located transverse process 198 and spinous process 197. Arrows V and D identify the ventral and dorsal directions, respectively. The spinal cord 191 itself is located within the dura mater 199, which also surrounds portions of the nerves exiting the spinal cord 191, including the ventral roots 192, dorsal roots 193, and dorsal root ganglia 194. The dorsal roots 193 enter the spinal cord 191 at the dorsal root entry region 187, and communicate with dorsal horn neurons located at the dorsal horn 186. In some embodiments, the first and second leads 111a, 111b are positioned just off the spinal cord midline 189 (e.g., about 1 mm offset) in opposing lateral directions so that the two leads 111a, 111b are spaced apart from each other by about 2 mm, as discussed above. In some embodiments, a lead or pairs of leads can be positioned at other locations, e.g., toward the outer edge of the dorsal root entry portion 187 as shown by a third lead 111c, or at the dorsal root ganglia 194, as shown by a fourth lead 111d, or approximately at the spinal cord midline 189, as shown by a fifth lead 111e.

In some embodiments the devices and systems of the present technology include features other than those described herein. For example, one lead 111 to six leads 111 can be positioned generally end-to-end at or near the patient's midline M and span vertebral levels from about T4 to about T12. In some embodiments, two, three, or four leads 111 are positioned end-to-end at or near the patient's midline from T4 to T12. In some embodiments, the leads 111 and/or other signal delivery devices can have locations other than those expressly shown herein. For example, one or more signal delivery devices can be positioned at the dorsal side of the spinal cord 191. In addition, the devices and systems of the present technology can include more than one internal stimulator and/or more than one external stimulator that can be configured for wireless stimulation, such as by using electromagnetic waves.

Several aspects of the technology are embodied in computing devices, e.g., programmed/programmable pulse generators, controllers and/or other devices. The computing devices on/in which the described technology can be implemented may include one or more central processing units, memory, input devices (e.g., input ports), output devices (e.g., display devices), storage devices, and network devices (e.g., network interfaces). The memory and storage devices are computer-readable media that may store instructions that implement the technology. In some embodiments, the computer readable media are tangible media. In some embodiments, the data structures and message structures may be stored or transmitted via an intangible data transmission medium, such as a signal on a communications link. Various suitable communications links may be used, including but not limited to a local area network and/or a wide-area network.

Figure 2:
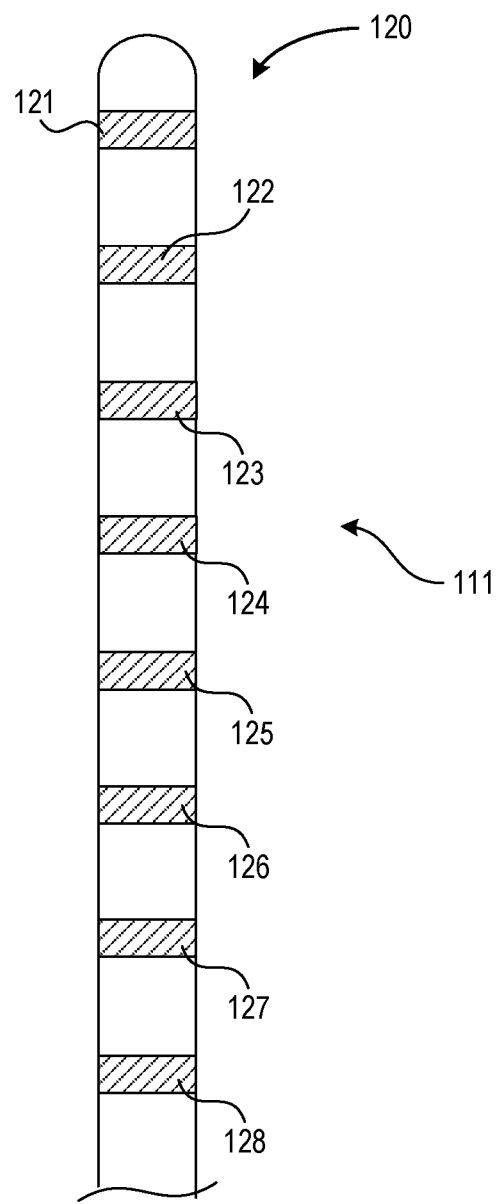
FIG. 2 is a schematic illustration of a representative lead body suitable for providing modulation to a patient in accordance with several embodiments of the present technology.

FIG. 2 is a partially schematic illustration of a representative lead body 111 that may be used to apply modulation to a patient in accordance with any of the foregoing embodiments. In general, the lead body 111 includes a multitude of electrodes or contacts 120. When the lead body 111 has a circular cross-sectional shape, as shown in FIG. 2, the contacts 120 can have a generally ring-type shape and can be spaced apart axially along the length of the lead body 111. In a particular embodiment, the lead body 111 can include eight contacts 120, identified individually as first, second, third . . . eighth contacts 121, 122, 123 . . . 128. In general, one or more of the contacts 120 are used to provide signals, and another one or more of the contacts 120 provide a signal return path. Accordingly, the lead body 111 can be used to deliver monopolar modulation (e.g., if the return contact is spaced apart significantly from the delivery contact), or bipolar modulation (e.g., if the return contact is positioned close to the delivery contact and in particular, at the same target neural population as the delivery contact). In still further embodiments, the pulse generator 101 (FIG. 1A) can operate as a return contact for monopolar modulation.

4.0 Representative Signals

FIG. 3A is a partially schematic illustration of a representative therapy signal 300a used to delivery therapy in accordance with embodiments of the present technology. The therapy signal 300a includes biphasic pulses 301a repeating in a continuous manner. Each individual pulse 301a includes an anodic pulse phase 302a, a cathodic pulse phase 304a, and an interphase interval 306a separating the anodic pulse phase 302a and the cathodic pulse phase 304a. In the illustrated embodiment, the anodic pulse phase 302a and the cathodic pulse phase 304a are symmetrical (e.g., having generally equal pulse widths and generally equal and opposite amplitudes) such that individual pulses 301a are charge balanced. Individual pulses 301a are separated by an interpulse interval 308a. Together, the pulse 301a and the interpulse interval 308a define a pulse period 310a. The pulse period 310a repeats in cycles that define a frequency of the therapy signal 300a.

The therapy signal 300a can have relatively long pulse widths, such as between about 5 ms and about 2 seconds. Accordingly, the anodic pulse phase 302a and the cathodic pulse phase 304a can each have a pulse width in a range of from about 5 ms to about 2 seconds. In embodiments for which the pulse 301a is a monophasic pulse, the monophasic pulse phase can have a pulse width between about 5 ms to about 2 seconds, or between about 5 ms and about 1 second, or between about 100 ms and about 1 second, or between about 100 ms and about 500 ms. Representative pulse widths include about 5 ms, about 10 ms, about 25 ms, about 50 ms, about 75 ms, about 100 ms, about 200 ms, about 300 ms, about 400 ms, about 500 ms, about 600 ms, about 700 ms, about 800 ms, about 900 ms, about 1 second, and/or about 2 seconds. In some embodiments, the pulse width is greater than about 5 ms, greater than about 10 ms, greater than about 25 ms, greater than about 50 ms, greater than about 75 ms, greater than about 100 ms, greater than about 500 ms, and/or greater than about 1 second. In the illustrated embodiment, the anodic pulse phase 302a and the cathodic pulse phase 304a have generally equal pulse widths that can offset charge build up in a signal delivery element (e.g., electrodes 120) and/or surrounding tissue. In other embodiments, and as described below with respect to FIG. 3B, the anodic pulse phase and cathodic pulse phase do not have the same pulse width. In yet other embodiments, the stimulation charge recovery is a passive process, in which a shunt resistance is connected across the active electrodes to allow for charge built up on the output and Helmholtz capacitances from the therapeutic pulse (e.g., the anodic pulse phase 302a) to 'bleed off'. In such embodiments, the therapy signal may be essentially a monophasic signal. As one skilled in the art will recognize, the frequency of the therapy signal 300a is based at least in part on the pulse width of the pulses 301a. For example, pulses with longer pulse widths typically (but not always) have lower frequencies. Accordingly, in some embodiments the frequency of the therapy signal 300a is less than about 100 Hz, less than about 10 Hz, less than about 5 Hz, and/or less than about 1 Hz.

The pulses 301a can have an amplitude (e.g., current amplitude or voltage amplitude) below the activation threshold of a target neuronal population. In such embodiments, the therapy signal 300a does not induce an action potential in target neurons when it is delivered to the target neuronal population. Generally, the activation of neurons depends on two variables: the strength (e.g., amplitude) of the signal and the duration (e.g., pulse width) for which the signal is applied. As the duration of the signal increases, the amplitude required to induce neuronal activation decreases. Accordingly, the amplitude of the pulses 301a is inversely related to the pulse width of the pulses 301a. In some embodiments, the amplitude remains below the rheobase of the target neuronal population. The rheobase refers to the minimum amplitude that results in neuronal activation when the therapy signal is applied for a continuous period (e.g., a period exceeding 100 ms, 200 ms, 300 ms, etc.). In some embodiments, the rheobase can be approximated by measuring the amplitude at which a patient exhibits the first clinically discernable effects of the signal. For example, in some embodiments, the amplitude of the pulses 301a is about 3 mA or less, such as between about 0.1 mA and about 2.5 mA or between about 0.5 mA and about 2 mA.

Use of relatively long pulse widths such as those described for the signal 300a shown in FIG. 3A can cause substantial charge to build up in the electrodes delivering the signal. Therefore, the pulse width and the amplitude of the pulse 301a can also be selected to remain below an acceptable charge and/or charge density for the electrode materials used to deliver the therapy signal 300a. As one skilled in the art will appreciate, exceeding the acceptable or "maximum" charge and/or charge density of the electrodes may cause electrolysis on the surface of the electrode, distort the therapy signal delivered by the electrode, increase corrosion of the electrode, shorten the expected lifespan of the electrode, and/or cause the electrode to emit materials or products that can damage the surrounding tissue. Accordingly, the pulse width and amplitude of the pulse 301a can be selected to deliver a therapeutically effective charge to the target neural population without causing one or more of the foregoing events associated with exceeding a maximum charge density of the electrode. Suitable electrode materials include platinum (e.g., platinum iridium) and other materials and alloys known in the art. For platinum electrodes, the pulse width and/or amplitude can be selected such that the charge density remains at or below about 300 $\mu C/cm^2$, which is currently a clinically acceptable maximum charge density for platinum electrodes. Table 1 below provides amplitude values that, for a set of particular pulse widths, generate a charge density of approximately 300 $\mu C/cm^2$ on a typical neurostimulation lead with electrodes of geometric surface area of approximately 12.7 $mm^2$.

TABLE 1

Signal Parameters for 300 $\mu C/cm^2$ Charge Density on an Electrode with Geometric Surface Area of 12.7 $mm^2$

| Pulse Width (ms) | Amplitude (mA) |
|---|---|
| 10 | 3.81 |
| 30 | 1.27 |
| 100 | 0.38 |
| 300 | 0.13 |
| 1000 | 0.04 |

The amplitude values in Table 1 are normalized to produce a 300 $\mu C/cm^2$ charge density at the recited pulse widths. The recited amplitude values therefore represent the "maximum" amplitude that, for the recited pulse widths, do not exceed the 300 $\mu C/cm^2$ charge density threshold. In embodiments in which the upper charge density threshold is a value other than 300 $\mu C/cm^2$, the corresponding amplitude values would change as well (assuming pulse width stays the same). For example, if the upper charge density threshold was greater than 300 $\mu C/cm^2$, the associated amplitude values would increase as well. In some embodiments, such as those described below with respect to FIGS. 5A and 5B, the maximum amplitude and/or upper charge density threshold that can be accommodated before inducing an event associated with exceeding a maximum charge density threshold for an electrode (e.g., waveform distortion, electrode surface bubbling, etc.) can be determined and used as the maximum amplitude and/or charge density threshold during waveform parameter selection.

In some embodiments, the pulse width and/or amplitude are selected such that the charge density approaches the maximum charge density permitted by the electrode material (e.g., within 5% of the maximum charge density, within 10% of the maximum charge density, within 20% of the maximum charge density, etc.). As described below, and without being bound by theory, applying the therapy signal 300a at an amplitude that is below the activation threshold of a target neuronal population but at an amplitude and pulse width combination that delivers relatively high charge densities is expected to directly suppress at least a subset of the target neuronal population. Because the native charge densities of polished electrodes can deliver sufficient charge over the relatively long pulse widths described herein, the electrodes do not necessarily require a coating material. However, in some embodiments, the electrodes nevertheless include a coating material (e.g., to increase the electrode surface area). The number of electrodes programmed to deliver the signal can also affect the total maximum charge. For example, in some embodiments, three electrodes are programmed as anodic and three electrodes are programmed as cathodic such that the total charge being delivered to the target neural population can be increased without exceeding the maximum charge density for any individual electrode.

In some embodiments, systems in accordance with the present technology include an algorithm that limits the stimulation charge to be below the acceptable charge and charge density for the electrode materials. Before delivering the therapy signal 300a, a user can input electrode information into a patient treatment system component (e.g., a graphical user interface on a modulator, controller, programmer, or other suitable device). In some embodiments, the electrode information is already stored in the patient treatment system, and/or the patient treatment system automatically calculates some or all of the electrode information. The electrode information can contain the electrode material, the surface area of the electrodes, and/or the number of electrodes (e.g., the number of anodes and the number of cathodes). In some embodiments, the surface area of the electrodes can be estimated from an impedance value associated with the electrode, which may be automatically detected by the system. For example, lower impedance values are associated with higher electrode surface areas. The user can then select a desired pulse width from a list or range of available pulse widths (e.g., between 5 ms and 2 seconds). Based at least in part on the selected pulse width and the electrode information, the algorithm can determine the upper limit of the programmable amplitude (e.g., the "maximum amplitude") based upon a calculation of maximum allowed charge density. For example, if a user inputs and/or the system determines that the electrodes are polished platinum iridium electrodes, the electrodes have a specific impedance value and/or surface area, and the pulse width is 30 ms, the algorithm can calculate the maximum amplitude that can be used without exceeding a charge density of 300 $\mu C/cm2$, which as reflected in Table 1 is about 1.27 mA.

In some embodiments, the maximum amplitude is below an activation threshold of a target neuronal population for the selected pulse width. For example, the maximum amplitude can be set below the rheobase of the first clinically discernable effect of the stimulation. As described in greater detail with respect to FIG. 4, the activation may be determined or approximated by slowly increasing the stimulation amplitude at a set pulse width (e.g., 5 ms) and asking the patient to report any sensory or physical perceptions from the stimulation. If the activation threshold has an amplitude value less than the maximum amplitude based on the charge density calculation, the activation threshold amplitude value can be entered into the patient treatment system (e.g., via the interface on the modulator, controller, or programmer) to set a new maximum amplitude for the therapy signal 300a.

FIG. 3B is a partially schematic illustration of another representative therapy signal 300b. Certain aspects of therapy signal 300b are generally similar to those described above with respect to the therapy signal 300a shown in FIG. 3A. For example, therapy signal 300b includes a pulse period 310b having a biphasic pulse 301b and an interpulse interval 308b. The pulse 301b has an anodic pulse phase 302b and a cathodic pulse phase 304b separated by an interphase interval 306b. Unlike the therapy signal 300a shown in FIG. 3A, however, the pulses 301b shown in FIG. 3B do not have symmetrical anodic pulse phases 302b and cathodic pulse phases 304b. Rather, the cathodic pulse phase 304b has a shorter pulse width and a greater amplitude than the anodic pulse phase 302b. In other embodiments, therapy signal 300b can have an anodic pulse phase 302b that has a shorter pulse width and a greater amplitude than the cathodic pulse phase 304b (e.g., a mirror image of therapy signal 300b). Regardless, the pulse width and amplitude of the cathodic pulse phase 304b can nevertheless be selected such that the total charge delivered in the anodic pulse phase 302b and the cathodic pulse phase 304b remains substantially equal to avoid having a charge build up in the electrode or the patient's tissue. In some embodiments, the amplitude of the anodic pulse phase 302b can remain below the activation threshold that results in the first clinically discernable effect of the stimulation (and/or below the rheobase). Similarly, the larger amplitude of the cathodic pulse phase 302b also remains below the threshold of a clinically discernable effect of stimulation (and/or below the rheobase). One expected advantage of therapy signal 300b is the recovery period takes less time, meaning the duration between subsequent anodic pulse phases 302b is less and the frequency of the pulse period 310b can be higher.

Figure 3C:
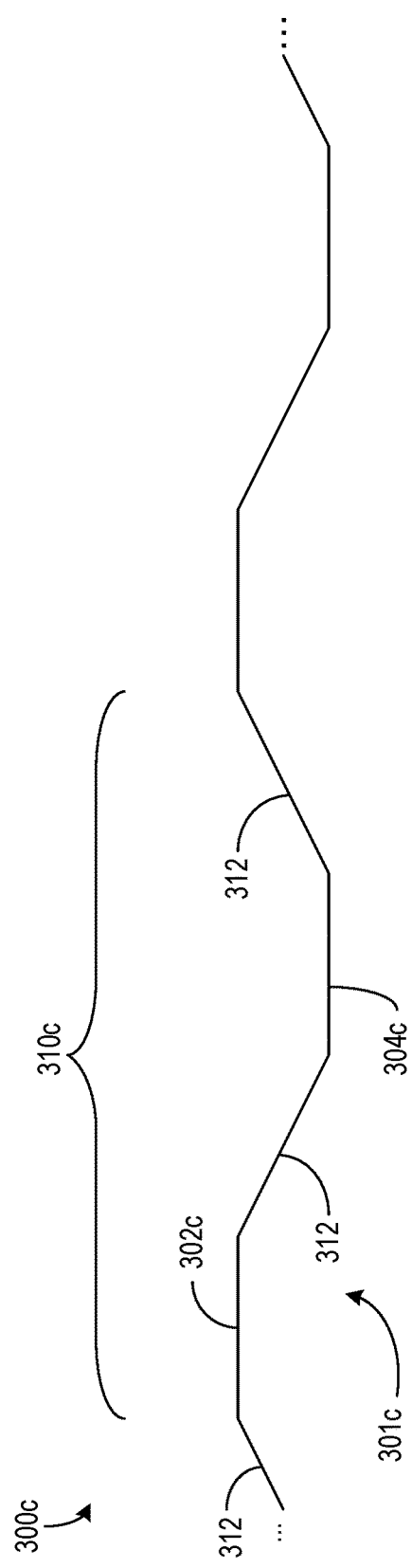

FIG. 3C illustrates a representative therapy signal 300c with a ramping period 312. The ramping period 312 transitions between a maximum amplitude of the anodic pulse phase 302c and a maximum amplitude of the cathodic pulse phase 304c. In some embodiments (e.g., as described below with respect to FIG. 3E), the anodic pulse phase 302c and the cathodic pulse phase 304c can include a portion of the ramping period 312. The ramping period 312 can have a duration that is substantially equal to the pulse width of the therapy signal 300c. For example, if the anodic pulse phase 302c and the cathodic pulse phase 304c each have a pulse width of about 100 ms, the ramping period 312 can have a duration of about 100 ms. Accordingly, the ramping period 312 can have a duration between about 5 ms and about 2 seconds. In other embodiments, the ramping period 312 is less than or greater than the pulse width of the anodic pulse phase 302c and/or the cathodic pulse phase 304c. Although the anodic pulse phase 302c and the cathodic pulse phase 304c are illustrated as symmetrical, the anodic pulse phase 302c and the cathodic pulse phase 304c can also have a configuration similar to that described above with respect to FIG. 3B, with the ramping period 312 extending therebetween.

Figure 3D:
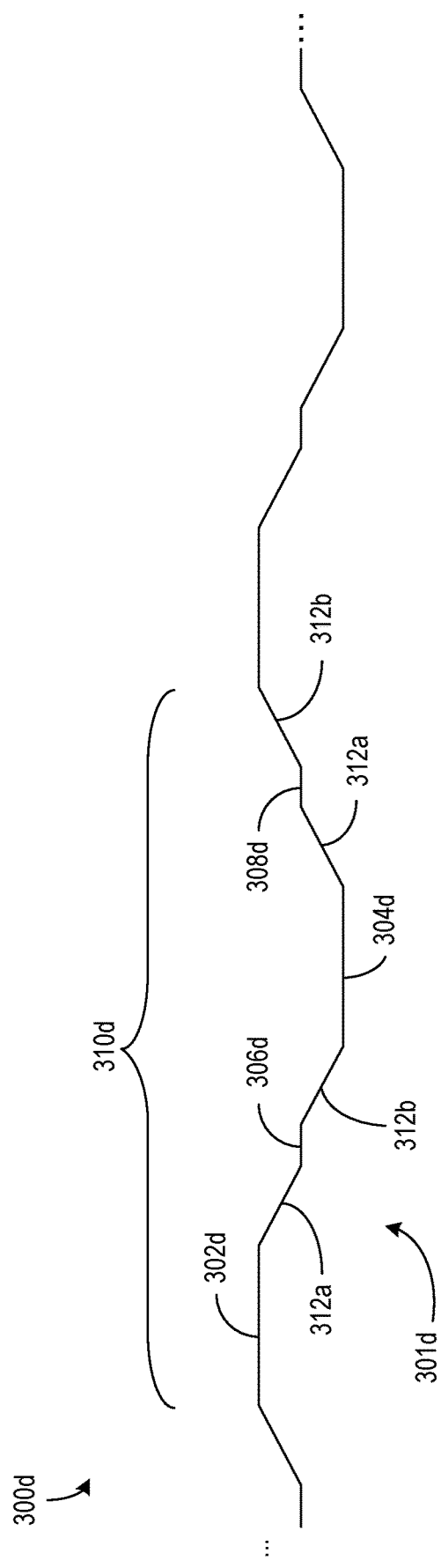

FIG. 3D illustrates another therapy signal 300d having a non-continuous ramping period 312 between the anodic pulse phase 302d and the cathodic pulse phase 304d during pulse period 310d. The noncontinuous ramping period can include a first ramping period 312a immediately following the anodic pulse phase 302d and the cathodic pulse phase 304d, and a second ramping period 312b immediately preceding the anodic pulse phase 302d and the cathodic pulse phase 304d. The first ramping period 312a and the second ramping period 312b can be separated by an interphase interval 306d (e.g., between an anodic pulse phase 302d and cathodic pulse phase 304d within the same pulse 301d) or an interpulse interval 308d (e.g., between adjacent pulses 301d). The first ramping period 312a and the second ramping period 312b can have the same or different durations. Together, the first ramping period 312a and the second ramping period 312b can have a duration substantially equal to the pulse width of the therapy signal 301d (e.g., between about 5 ms and about 2 seconds). In other embodiments, the first ramping period 312a and the second ramping period 312b together have a duration that is less than or greater than the pulse width of the therapy signal 301d.

Figure 3E:
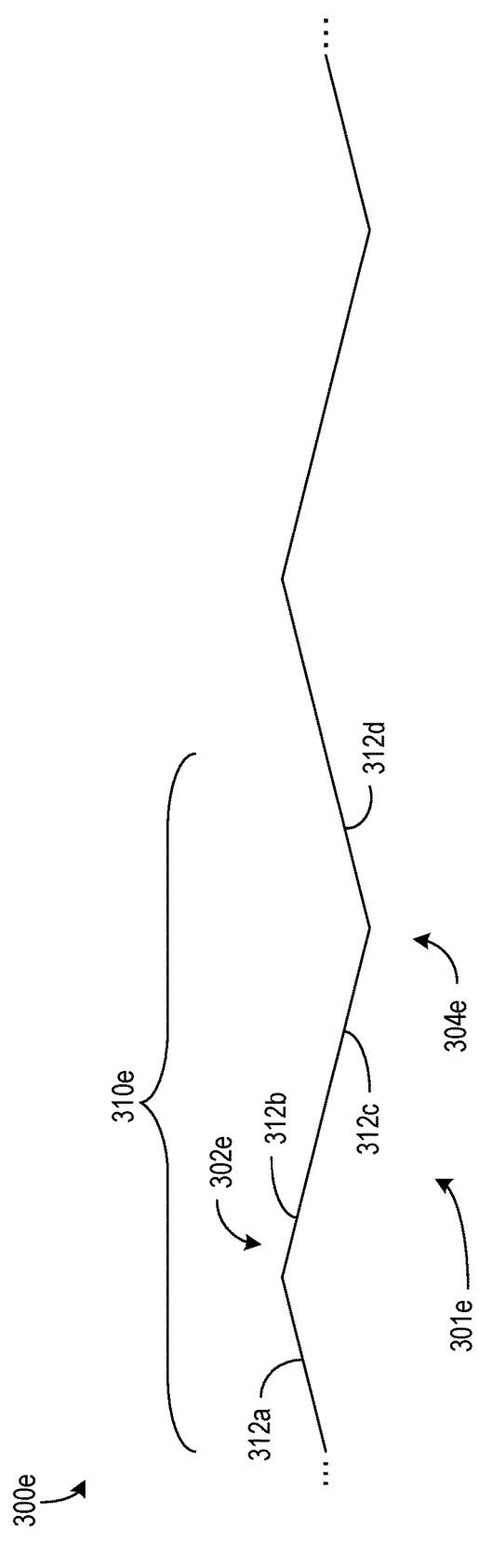

As indicated above, some embodiments of the present technology include therapy signals having ramped, or at least partially ramped, anodic pulse phases and/or ramped, or at least partially ramped, cathodic pulse phases. For example, FIG. 3E illustrates a representative ramped therapy signal 300e in which the therapy signal 300e includes an anodic pulse phase 302e having a first ramping period 312a and a second ramping period 312b, and a cathodic pulse phase 304e having a third ramping period 312c and a fourth ramping period 312d. As described above, the anodic pulse phase 302e may have a pulse width of between about 5 ms and about 2 seconds, and the cathodic pulse phase 304e may have a pulse width of between about 5 ms and about 2 seconds. The second ramping period 312b can immediately follow the first ramping period 312a, as illustrated in FIG. 3E, or the second ramping period 312b can be spaced apart from the first ramping period 312a by a period of the anodic pulse phase 302a having a constant amplitude (e.g., as illustrated in FIG. 3C). Likewise, the fourth ramping period 312d can immediately follow the third ramping period 312c, as also illustrated in FIG. 3E, or the fourth ramping period 312d can be spaced apart from the third ramping period 312c by a period of the cathodic pulse phase 304a having a constant amplitude (e.g., as illustrated in FIG. 3C). In the illustrated embodiment, the second ramping phase 312b of the anodic pulse phase 302e immediately transitions into the third ramping period 312c of the cathodic pulse phase 304e. However, in other embodiments the second ramping period 312b of the anodic pulse phase 302e can be separated from the third ramping period 312c of the cathodic pulse phase 304e by an interphase interval (e.g., as illustrated in FIG. 3D). In the illustrated embodiment, the pulse period 310e is equal to the duration of the pulse 301e. However, in other embodiments respective pulses 301e can be separated by an interpulse interval (e.g., the fourth ramping period 312d can be separated from the first ramping period 312a).

Figure 3F:
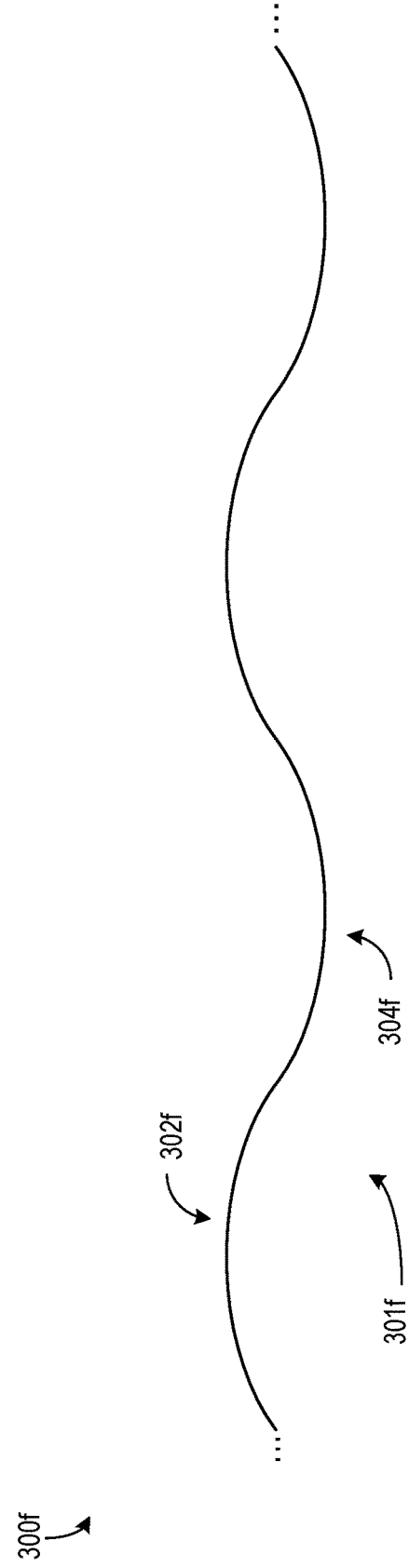

FIG. 3F illustrates another representative therapy signal 300f used to deliver therapy in accordance with embodiments of the present technology. Unlike the therapy signals 300a-300e of FIGS. 3A-3E, which have a square wave form, a ramped wave form, or a combination thereof, the therapy signal 300f of FIG. 3F has a sinusoidal wave form pattern (or other non-linear pattern) comprising repeating curved pulses 301f. Each individual pulse 301f has an anodic pulse phase 302f and a cathodic pulse phase 304f. Similar to the signals 300a-300e described above, the anodic pulse phase 302f may have a pulse width between about 5 ms and about 2 seconds, and the cathodic pulse phase 304f may have a pulse width between about 5 ms and about 2 seconds.

Each of therapy signals 300a-f is expected to globally or at least partially suppress target neurons (e.g., NS and WDR neurons in the superficial dorsal horn pain circuits) when delivered to a patient's spinal cord region. As described above, suppressing the target neurons is expected to inhibit or otherwise reduce the transmission of pain signals to the brain. In some embodiments, the therapy signals 300a-f are expected to preferentially suppress hyperactive neurons, such as those that may be responsible for a patient's pain.

Figure 3G:
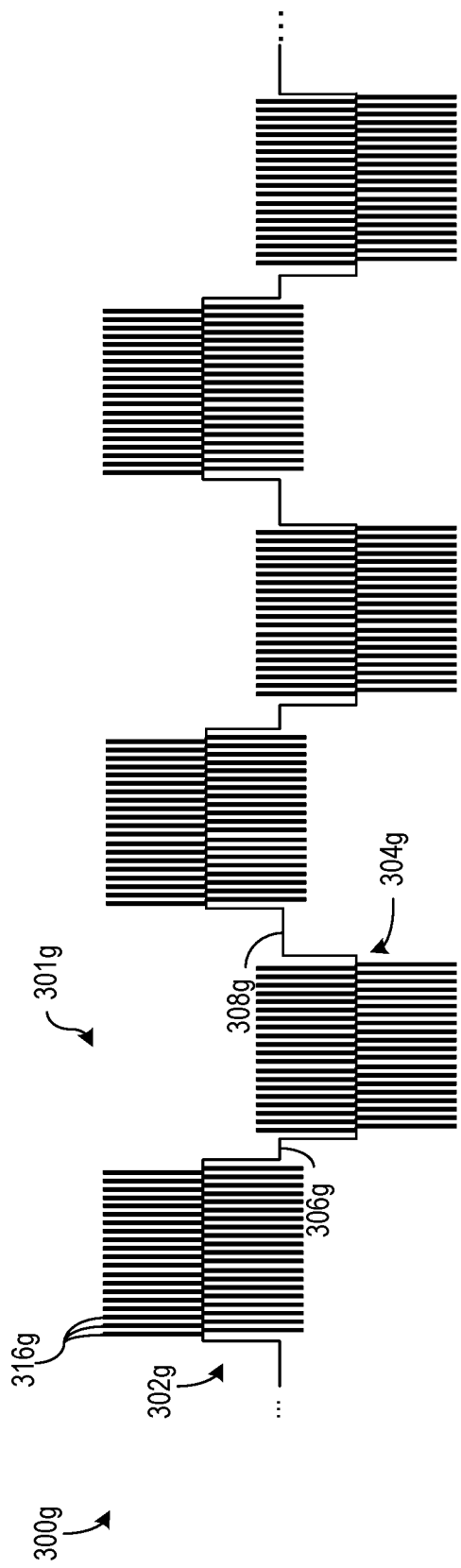

Any of the signals 300a-f described above may further include offset high frequency pulses and/or bursts of high frequency pulses occurring during the anodic and/or cathodic pulse phases (e.g., pulses starting and ending at the non-zero amplitudes of the anodic and cathodic pulse phases). For example, FIG. 3G illustrates a representative signal 300g that is generally similar to the therapy signal 300a shown in FIG. 3A but further includes high frequency pulses 316g occurring during the anodic pulse phase 302g and the cathodic pulse phase 304g of the pulse 301g. As illustrated, the high frequency pulses 316g generally occur during the anodic pulse phase 302g and/or the cathodic pulse phase 304g, but are generally absent during the interphase interval 306g and the interpulse interval 308g. Although shown as occurring during both the anodic pulse phase 302g and the cathodic pulse phase 304g, in other embodiments, the high frequency pulses 316g occur only during the anodic pulse phase 302g. In yet other embodiments, the high frequency pulses 316g occur only during the cathodic pulse phase 304g.

The high frequency pulses 316g can have a frequency in a frequency range of from about 1.2 kHz and about 100 kHz. For example, the high frequency pulses 316g can have a frequency in a frequency range of from about 1.2 kHz to about 50 kHz, from about 1.2 kHz to about 25 kHz, from about 3 kHz to about 15 kHz, or from about 5 kHz to about 15 kHz. In some embodiments, the high frequency pulses 316g have a frequency of about 5 kHz, about 10 kHz, about 15 kHz, about 20 kHz, about 25 kHz, about 50 kHz, or about 100 kHz. The high frequency pulses 316g can have a pulse width in a pulse width range of from about 10 microseconds to about 333 microseconds, from about 25 microseconds to about 166 microseconds, from about 33 microseconds to about 100 microseconds, or from about 50 microseconds to about 166 microseconds. In some embodiments, such as the embodiment illustrated in FIG. 3G, the high frequency pulses 316g have an amplitude that is greater than the amplitude of the underlying anodic pulse phase 302g and/or the cathodic pulse phase 304g. In other embodiments, the high frequency pulses 316g have an amplitude that is equal to or less than the amplitude of the anodic pulse phase 302g and/or the cathodic pulse phase 304g. Further yet, although shown as bi-phasic pulses, the high frequency pulses 316g may instead be monophasic pulses. The high frequency pulses 316g can also have a ramped and/or sinusoidal shape.

The anodic pulse phase 302g may have an overall pulse width between about 5 ms and about 2 seconds (not accounting for any phase change during the high frequency pulses 316g), as described in detail above for the signal 300a of FIG. 3A. Likewise, the cathodic pulse phase 304g may also have an overall pulse width between about 5 ms and about 2 seconds (not accounting for any phase change during the high frequency pulses 316g).

The therapy signal 300g can be described as having a base component (e.g., base component pulses or low frequency pulses having the anodic pulse phase 302g and the cathodic pulse phase 304g) and a high frequency component (e.g., the high frequency pulses 316g). The base component may also be referred to as a low frequency component. In some embodiments, the base component and the high frequency component are a single waveform, and therefore are generally administered using the same electrodes/contacts. In other embodiments, the high frequency component is superimposed over the base component to create the therapy signal 300g.

Figure 3H:
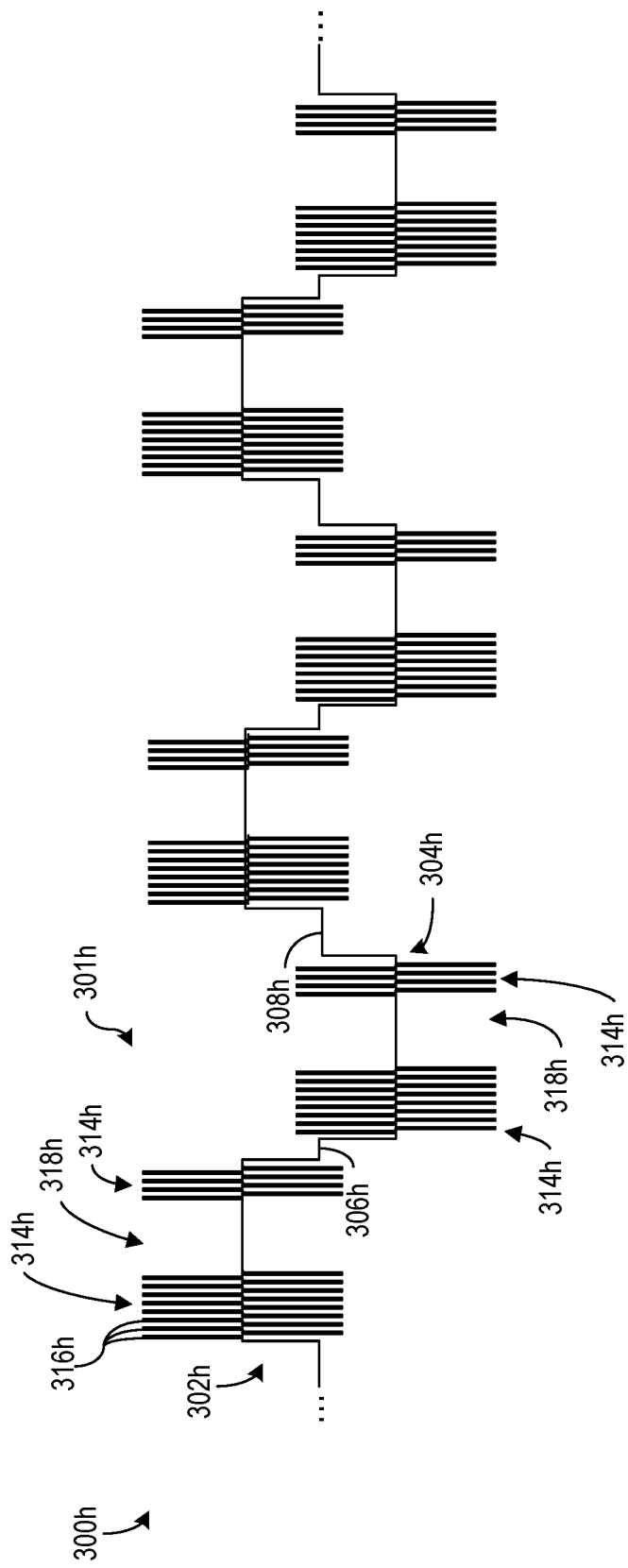

FIG. 3H illustrates another representative signal 300h used to deliver therapy in accordance with embodiments of the present technology. The signal 300h is generally similar to the signal 300g shown in FIG. 3G, but instead of delivering high frequency pulses during the entirety of (or at least approximately the entirety of) the anodic pulse phase and the cathodic pulse phase, the signal 300h includes high frequency pulse bursts 314h ("the bursts 314h") occurring during only portions of the anodic pulse phase 302h and the cathodic pulse phase 304h of the pulse 301h. Sequential bursts 314h are separated by a quiescent period 318h. As illustrated, the bursts 314h generally occur during the anodic pulse phase 302h and/or the cathodic pulse phase 304h, but are generally absent during the interphase interval 306h and the interpulse interval 308h. Although shown as occurring during both the anodic pulse phase 302h and the cathodic pulse phase 304h, in other embodiments, the bursts 314h occur only during the anodic pulse phase 302h. In yet other embodiments, the bursts 314h occur only during the cathodic pulse phase 304h.

The bursts 314h include one or more individual high frequency pulses 316h repeating at an intra-burst frequency in a frequency range of from about 1.2 kHz and about 100 kHz, from about 1.2 kHz to about 50 kHz, from about 1.2 kHz to about 25 kHz, from about 3 kHz to about 15 kHz, or from about 5 kHz to about 15 kHz. In some embodiments, the intra-burst frequency of the high frequency pulses 316h is about 5 kHz, about 10 kHz, about 15 kHz, about 20 kHz, about 25 kHz, about 50 kHz, or about 100 kHz. The high frequency pulses 316h can have a pulse width in a pulse width range of from about 10 microseconds to about 333 microseconds, from about 25 microseconds to about 166 microseconds, from about 33 microseconds to about 100 microseconds, or from about 50 microseconds to about 166 microseconds. In some embodiments, such as the embodiment illustrated in FIG. 3H, the high frequency pulses 316h have an amplitude that is greater than the amplitude of the underlying anodic pulse phase 302h and/or the cathodic pulse phase 304h. In other embodiments, the high frequency pulses 316h have an amplitude that is equal to or less than the amplitude of the anodic pulse phase 302h and/or the cathodic pulse phase 304h. Further yet, although shown as bi-phasic pulses, the high frequency pulses 316h may instead be monophasic pulses. The high frequency pulses 316h can also have a ramped and/or sinusoidal shape.

Each sequential burst of the high frequency pulse bursts 314h can include the same or a different number of individual high frequency pulses 316h, compared to the preceding burst 314h. For example, in the illustrated embodiment, the bursts 314h are shown as having either eight or four individual high frequency pulses 316h. In other embodiments, other numbers of high frequency pulses 316h can be delivered during the bursts 314h.

The anodic pulse phase 302h may have an overall pulse width between about 5 ms and about 2 seconds (not accounting for any phase change during the bursts 314h), as described in detail above for the signal 300a of FIG. 3A. Likewise, the cathodic pulse phase 304h may also have an overall pulse width between about 5 ms and about 2 seconds (not accounting for any phase change during the bursts 314h).

As with the therapy signal 300g of FIG. 3G, the therapy signal 300h of FIG. 3H can also be described as having a base component (e.g., the anodic pulse phase 302h and the cathodic pulse phase 304h) and a high frequency component (e.g., burst 314h of high frequency pulses 316h). In some embodiments, the base component and the high frequency component are a single waveform. In other embodiments, the high frequency component is superimposed over the base component to create the therapy signal 300h.

Figure 4:
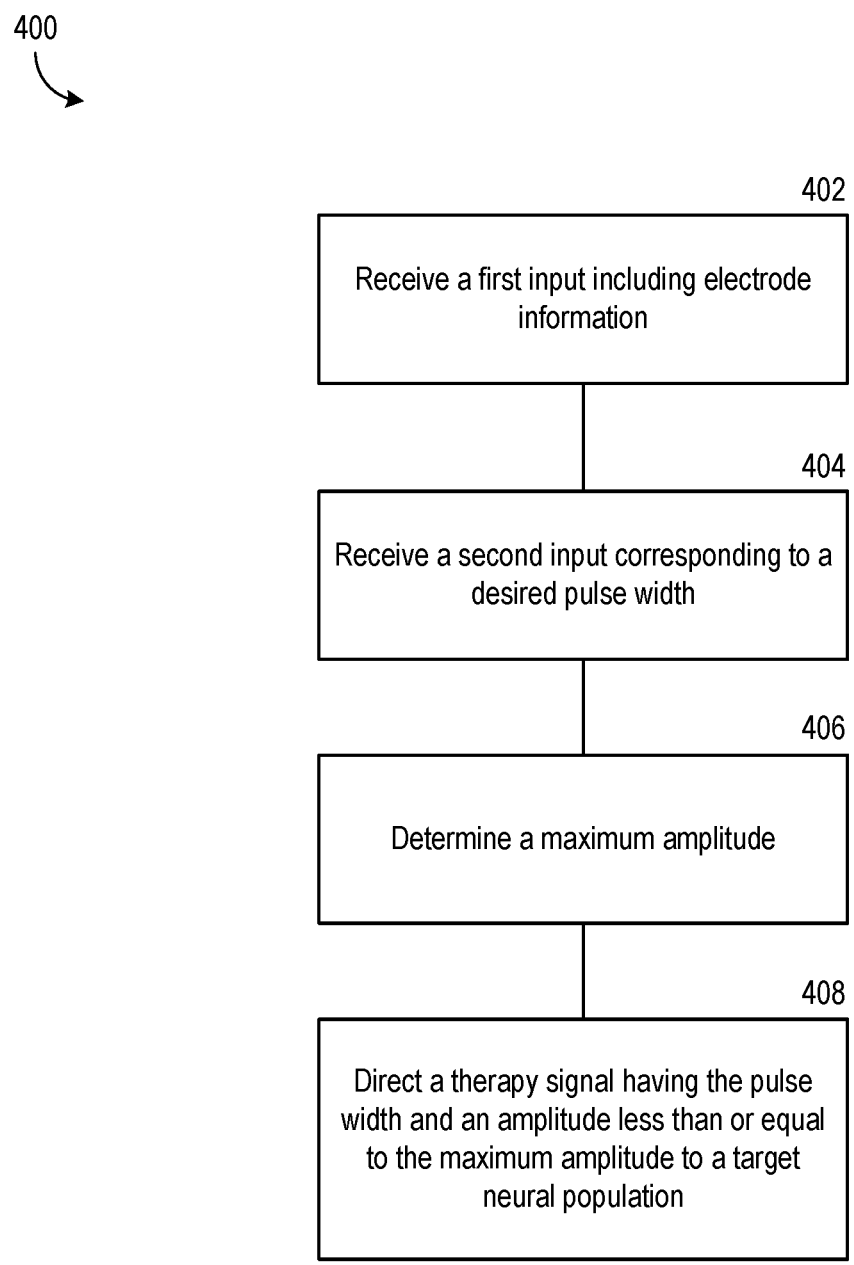
FIG. 4 is a flow diagram illustrating a method for treating a patient in accordance with embodiments of the present technology.

FIG. 4 is a block diagram illustrating a method 400 for treating a patient in accordance with embodiments of the present technology. Some or all of the steps in the method 400 can be performed by a processor executing instructions stored on or more elements of a patient treatment system. The method 400 can include receiving a first input including electrode information (step 402). The electrode information can relate to certain characteristics of one or more electrodes of the patient treatment system that are implanted in, or implantable into, the patient for delivering an electrical signal to a target neural population. In particular, the electrode information can include, among other things, the electrode material, the surface area of the electrode, and/or the number of electrodes. In addition to or in lieu of the surface area, the electrode information can include impedance values associated with the one or more electrodes. If impedance values are received, the method 400 can optionally include calculating the surface area based at least in part on the impedance values. The first input can be received from a user inputting the electrode information into a graphical user interface or other suitable means included as part of the patient treatment system, such as a modulator, controller, programmer, or other suitable device. In some embodiments, the first input can be received by accessing a memory storing the electrode information. In addition, one or more of the foregoing inputs can be received/retrieved from a computer-readable storage medium, and/or otherwise generated without a direct user input.

The method 400 can continue by receiving a second input corresponding to a desired pulse width (step 404). The second input can also be received from a user inputting the electrode information into the graphical user interface or other suitable device. In some embodiments, the graphical user interface can include a list of available pulse widths (e.g., ranging from 5 ms to 2 seconds) and the input corresponds to a user selecting one of the available pulse widths. In other embodiments, the user can directly input a desired pulse width without selecting from a list of available pulse widths. In yet other embodiments, the patient treatment system may automatically select or recommend a pulse width.

Based at least in part on the electrode information and the pulse width, the processor can calculate a maximum amplitude that can be delivered without exceeding the maximum charge density of the electrodes and/or inducing events associated with exceeding the maximum charge density of the electrodes (e.g., using the algorithm described above with respect to FIG. 3A) (step 406). In some embodiments, the maximum amplitude can be determined by testing the waveform having the selected pulse width at incremental amplitudes until an event associated with exceeding the maximum charge density of the electrodes is observed, as described later with respect to FIGS. 5A and 5B. The maximum amplitude may also be set to avoid exciting the target neuronal tissue (e.g., the maximum amplitude can be below an activation threshold of the neurons). To determine the maximum amplitude that avoids exciting the target neuronal tissue, a signal with the selected pulse width can be delivered to the patient via the electrodes, and the amplitude can be increased (e.g., incrementally or continuously) until either (i) the maximum amplitude based on the charge density calculation is reached, or (ii) a clinically discernable effect other than the therapeutic effect of the therapy signal is observed in the patient. If the maximum amplitude based on the charge density calculation is reached before a clinically discernable effect other than the therapeutic effect of the therapy signal is observed, the maximum amplitude remains unchanged. If, however, the amplitude at which the clinically discernable effect is observed is less than the maximum amplitude based on the charge density calculation, the amplitude at which the clinically discernable effect is observed can be set as the new maximum amplitude. In other embodiments, the amplitude at which the clinically discernable effect is observed can be determined before calculating the maximum amplitude based on the charge density calculation.

The method 400 can continue by directing a therapy signal having the pulse width and an amplitude less than or equal to the maximum amplitude to the target neural population (step 408). For example, the modulator, controller, or programmer can direct a pulse generator to generate the therapy signal and deliver, via the electrodes, the therapy signal to the target neural population. Without being bound by theory, the therapy signal directly suppresses the target neurons to reduce the patient's pain.

Other suitable methods for delivering the therapy signals described herein can also be used. In some embodiments, the steps of receiving the electrode information and determining a maximum amplitude based on the maximum charge density can be omitted. In such embodiments, a pulse width is selected and various amplitudes are tested to determine a maximum amplitude beyond which the patient begins to exhibit a clinically discernable effect. The signal can then be applied at an amplitude less than the determined maximum amplitude. The therapy signals described herein can also be applied in combination with other therapies, such as high frequency SCS or conventional SCS.

Figure 5A:
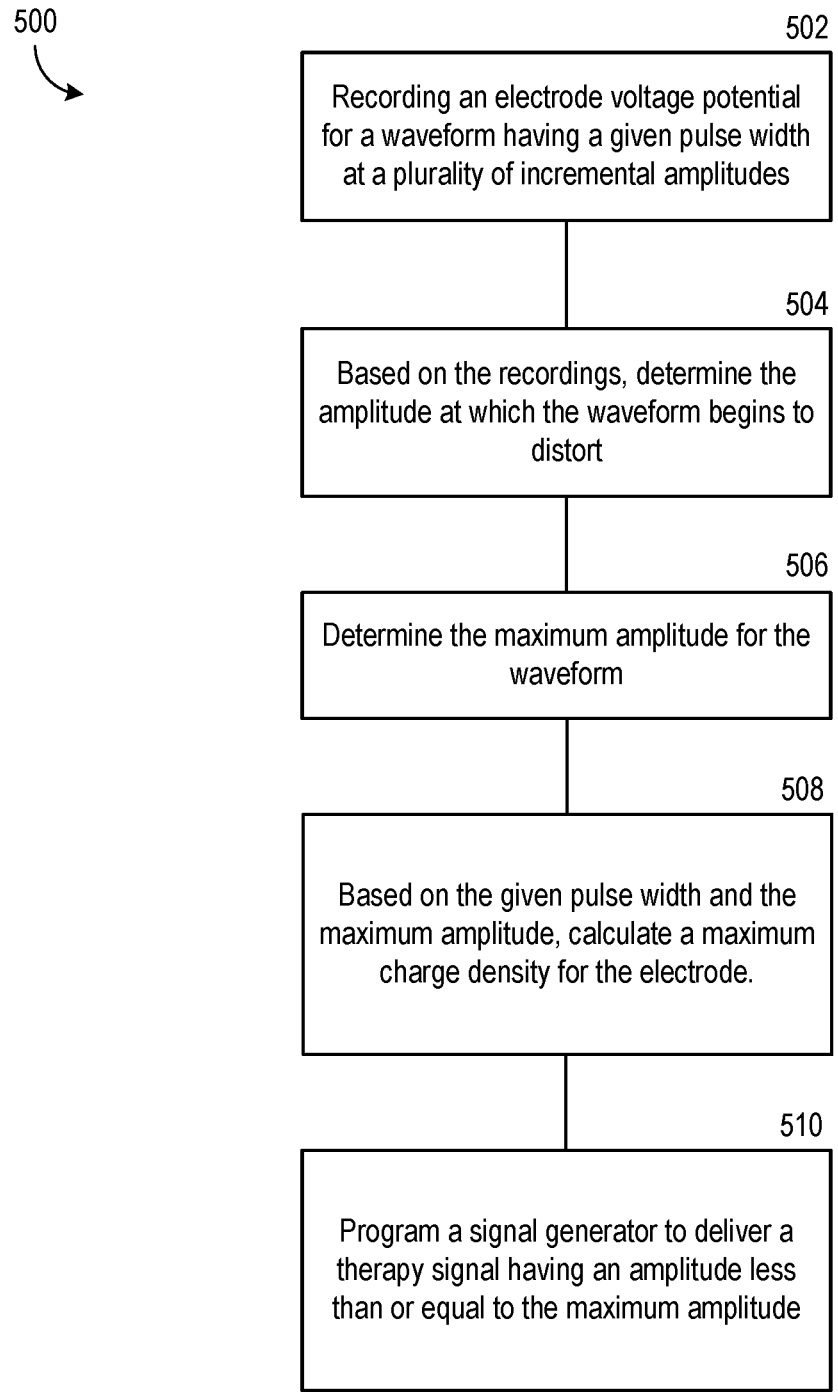
FIG. 5A is a flow diagram illustrating a method for determining a maximum amplitude for a waveform having a given pulse width in accordance with embodiments of the present technology.
Figure 5B:
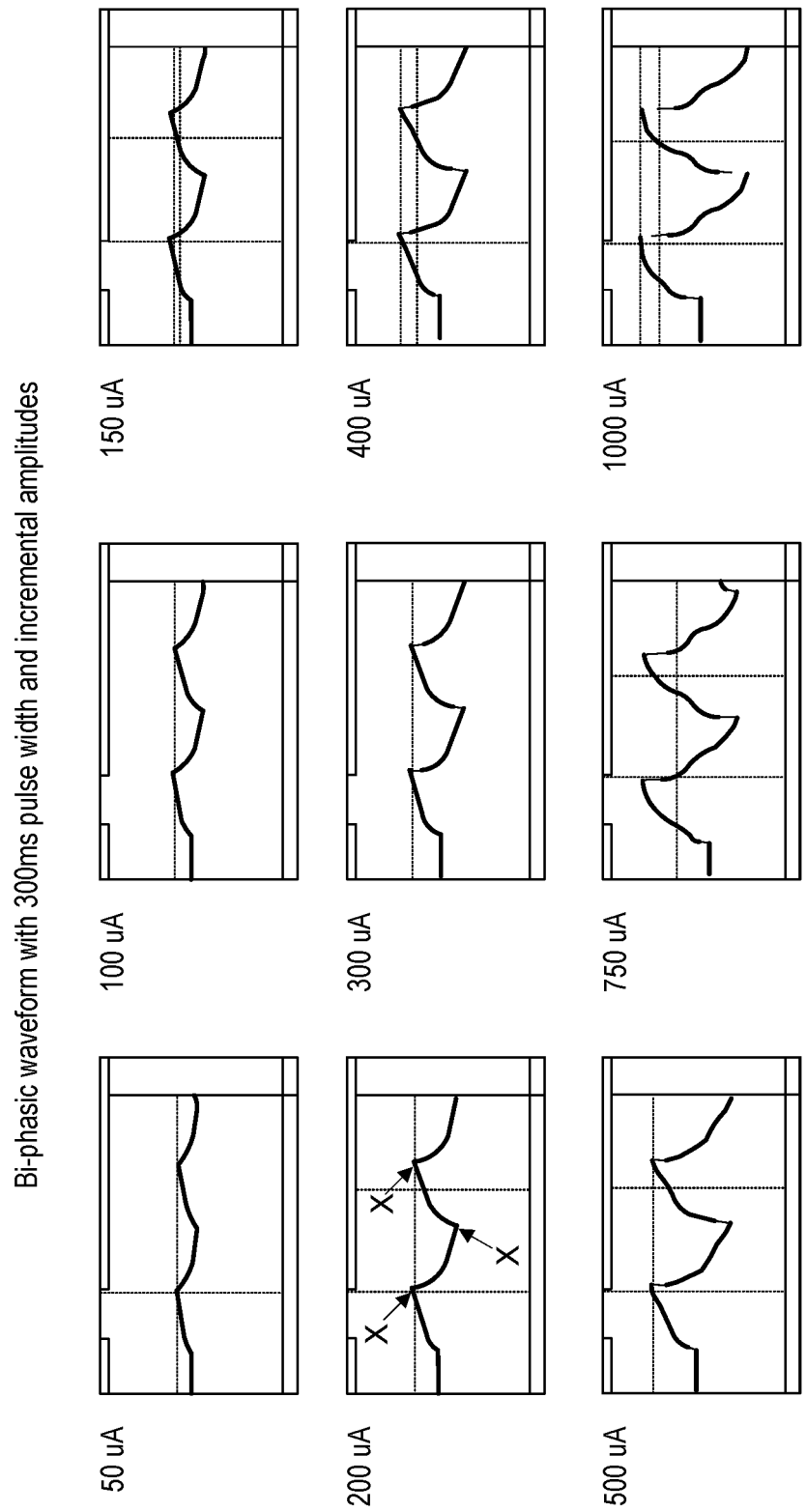
FIG. 5B is a series of scope traces for determining the maximum amplitude for a waveform having a given pulse width in accordance with the method shown in FIG. 5A.

As indicated above, the present technology further includes techniques for determining a maximum amplitude that can be delivered at a given pulse width. For example, FIG. 5A is a flowchart of a method 500 for determining a maximum amplitude at which a waveform having a given pulse width can be administered, without distorting the waveform. The method can begin in step 502 by recording the voltage potential of an electrode outputting a waveform having a given pulse width at a plurality of incremental amplitudes. This may include selecting a pulse width (e.g., 10 microseconds, 30 microseconds, 100 microseconds, 300 microseconds, 1,000 microseconds, etc.) and recording a trace (e.g., a measurement of the electrode voltage over time, as might be observed on an oscilloscope trace) of the waveform having the selected pulse width at the plurality of incremental amplitudes. The increment may include a stepwise increment, with each subsequent amplitude increasing by a common amount (e.g., 100 µA) relative to a preceding amplitude. In other embodiments, the increment between subsequent amplitudes may be variable. FIG. 5B provides an example of a plurality of voltage potential traces recorded using a voltage measurement system (in this case, an oscilloscope) for a waveform having a pulse width of 300 microseconds. The scope traces were recorded at incremental amplitudes of 50 µA, 100 µA, 150 µA, 200 µA, 300 µA, 400 µA, 500 µA, 750 µA, and 1,000 µA. In some embodiments, the voltage can be measured at step 502 on the surface of the electrode being tested, via another electrode positioned adjacent the electrode being tested, via a register connected in series between a pulse generator and the electrode being tested, or another suitable recording technique.

Returning to FIG. 5A, the method 500 can continue in step 504 by determining, based on the recordings taken in step 502, the amplitude at which the waveform begins to distort. This may include, for example, manually or automatically analyzing the morphology of the voltage potential or other recordings measured in step 502 to identify waveform distortion. In some embodiments, waveform distortion may present as a reversal or inflection in the slope of the waveform in the voltage potential as the voltage potential increases (e.g., which may be referred to as a "shoulder"). The amplitude at which the shoulder or inflection appears is therefore the amplitude at which waveform distortion begins. In FIG. 5B, for example, the shoulder (identified by the arrows marked "x") is first observed in the voltage potential trace of the waveform at an amplitude of 200 µA. In some embodiments, determining the amplitude at which the waveform distorts can include identifying a reversal or inflection in the slope that exceeds a minimum threshold to account for any potential noise in the signal.

The method 500 can continue in step 506 by determining (e.g., selecting) the maximum amplitude for the waveform based at least in part on the determination made in step 504. For example, the maximum amplitude can be set as the largest tested amplitude that does not induce waveform distortion. In FIG. 5B, for example, the largest tested amplitude at which waveform distortion does not occur is 150 µA. Thus, 150 µA could be selected as the maximum amplitude. Optionally, determining the maximum amplitude can include testing a plurality of additional incremental amplitudes between the amplitude determined in step 504 and the amplitude determined in step 506 to further "fine tune" the maximum amplitude. For example, in the embodiment shown in FIG. 5B, steps 502, 504, and 506 could be repeated for a plurality of incremental amplitudes between 150 µA and 200 µA.

Once the maximum amplitude is determined in step 506, the method 500 can optionally continue in step 508 by calculating the maximum charge density based on the maximum amplitude determined in step 504. This may be done by multiplying the pulse width and the amplitude to obtain the charge per phase of the waveform, and then dividing the charge per phase by the electrode surface area.

For patient safety, steps 502-506 of the method 500 are generally performed with the electrode in a saline bath or other suitable environment rather than with the electrode implanted in a patient. However, once the maximum amplitude is determined in step 506 and/or the maximum charge density is determined in step 508, the method 500 can continue in step 510 by programming a signal generator to deliver a therapy signal having an amplitude less than or equal to the maximum amplitude to a target neural population in a patient's spinal cord region.

Of note, waveform distortion is often the first adverse effect of exceeding a maximum charge density threshold of an electrode. Thus, while other adverse effects (e.g., electrode bubbling, electrode corrosion, etc.) can occur if the maximum charge density is exceeded, such events usually occur at amplitudes that are greater than the amplitude at which waveform distortion occurs. Thus, using waveform distortion to set the maximum amplitude threshold is also expected to prevent the other adverse effects identified herein that are associated with exceeding a maximum charge density of an electrode.

5.0 Representative Results from Animal Studies

Figure 6:
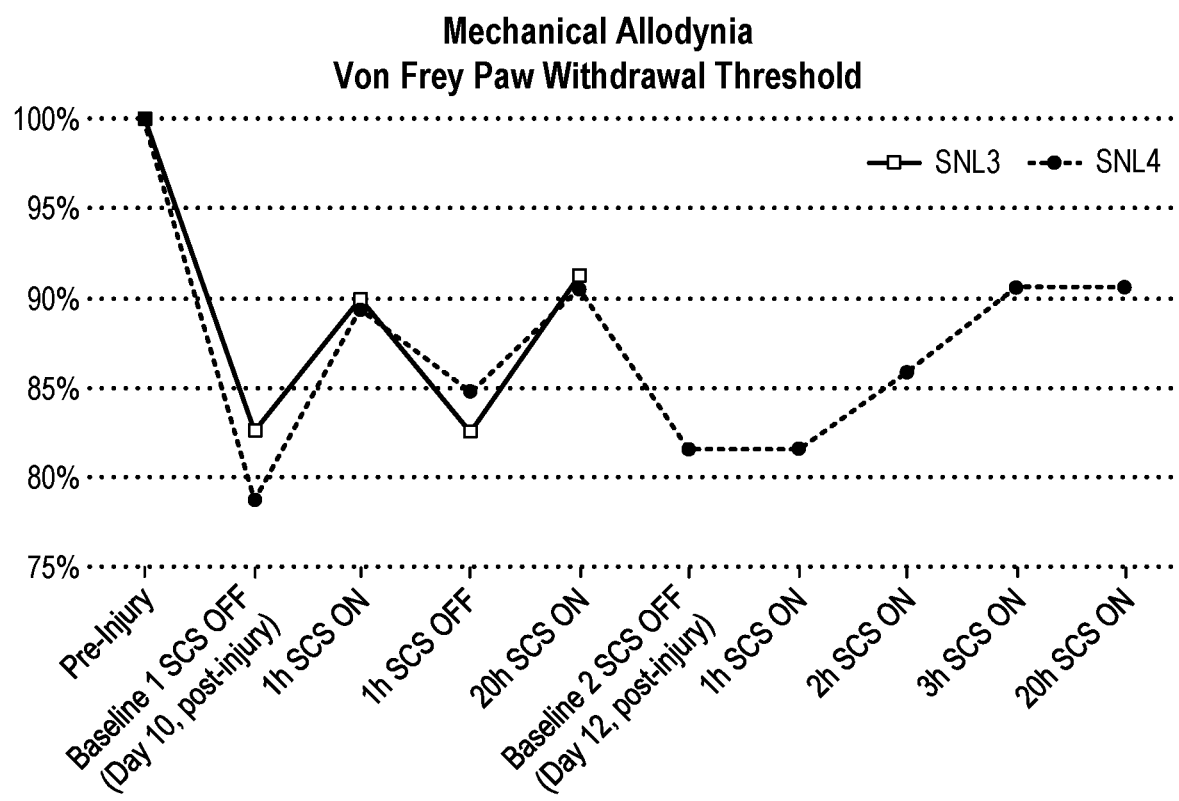
FIG. 6 is a graph demonstrating the effect of an SCS therapy signal having relatively long pulse widths on an animal pain model.

The assignee of the present application, Nevro Corp., has conducted preliminary animal studies to demonstrate the effect of therapy signals having relatively long pulse widths, such as those described herein. In a first study, the effectiveness of a signal having relative long pulse widths was tested on rats with surgically-induced allodynia. In particular, two rats underwent spinal nerve ligation (SNL) to induce mechanical sensitivity (allodynia) in the rats. The effect of SCS using therapy signals with relatively long pulse widths was then assessed using von Frey (vF) paw withdrawal testing, as compared to (a) pre-SNL vF testing, and (b) post-SNL vF testing during periods without SCS application. The SCS was applied as a 0.5 kHz sine wave (i.e., the anodic pulse phase had a pulse width of 1 second and the cathodic pulse phase had a pulse width of 1 second) with a 150-200 µA fixed amplitude. FIG. 6 is a graph depicting the behavioral response (i.e. paw withdrawal threshold) of the rats to the vF testing. As shown, the paw withdrawal threshold decreased approximately 20% as a result of the SNL surgery, but was restored by about half during application of SCS. This indicates that SCS with relatively long pulse widths reduced the allodynia in the rats.

In another animal study, three different SCS therapy signals were tested to determine the impact of the therapy signals on the electrophysiological response of rat spinal neurons to increasing nociceptive vF stimuli. The first therapy signal was a bi-phasic signal having an anodic phase pulse width of 1 second, a cathodic phase pulse width of 1 second, and an amplitude of 150-200 µA (e.g., generally similar to the therapy signal 300a shown in FIG. 3A), the second therapy signal was a high frequency bi-phasic signal having a frequency of 10 kHz, and the third therapy signal was a bi-phasic signal having an anodic phase pulse width of 300 ms, a cathodic phase pulse width of 300 ms, and offset 10 kHz high frequency pulses occurring during the anodic and cathodic pulse phases (e.g., generally similar to the therapy signal 300g described with respect to FIG. 3A). Nociceptive vF stimuli of increasing intensity were administered to the rats during application of the first signal, the second signal, the third signal, and in the absence of any SCS signal. The neuron firing rate evoked in response to the nociceptive vF stimuli was then measured.

Figure 7A:
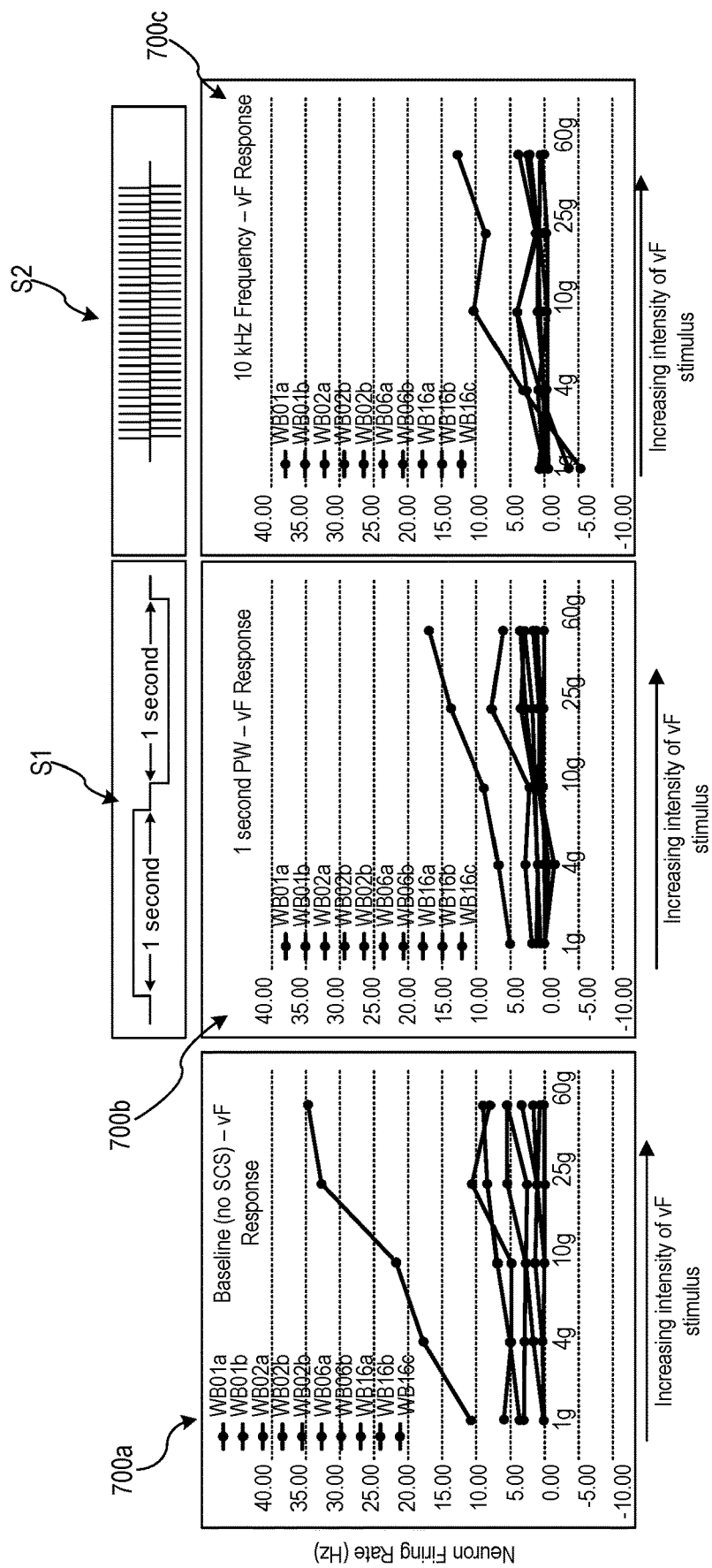
FIGS. 7A-7C are graphs comparing the suppressive effect of several SCS therapy signals on neuron firing rate evoked by nociceptive stimuli.

FIG. 7A depicts the neuron firing rate evoked in ten different neurons of a first animal in response to the vF stimuli during application of the first signal, the second signal, and in the absence of any SCS signal. More specifically, FIG. 7A includes a first graph 700a illustrating the neuronal firing rate evoked by vF stimuli of various intensities in the absence of any SCS, a second graph 700b illustrating the neuronal firing rate evoked by vF stimuli of various intensities during application of the first signal (shown as S1 in FIG. 7A), and a third graph 700c illustrating the neuronal firing rate evoked by vF stimuli of various intensities during application of the second signal (shown as S2 in FIG. 7A). The evoked neuronal responses shown in the graphs 700a-c are determined as the difference between the neuronal activity immediately following application of the vF stimulus and the neuronal activity immediately preceding application of the vF stimulus, with each line representing an individual neuron's response. A "flatter" line therefore represents a relatively smaller increase in evoked response as the vF stimulus intensity is increased, whereas a "steeper" line represents a larger increase in evoked response as the vF stimulus intensity is increased. Although one neuron appeared to be more active than the others, the general response of the neurons to stimuli of increasing intensity can be observed from graphs 700a-700c. As illustrated, both the second graph 700b and the third graph 700c show a generally flatter evoked neural response (compared to the first graph 700a) as the vF stimuli was increased in intensity. Accordingly, both the first signal S1 and the second signal S2 partially suppressed the neuronal firing evoked by the nociceptive vF stimulus (e.g., each signal at last partially suppressed the neurons) relative to the neuronal firing evoked in the absence of SCS.

Figure 7B:
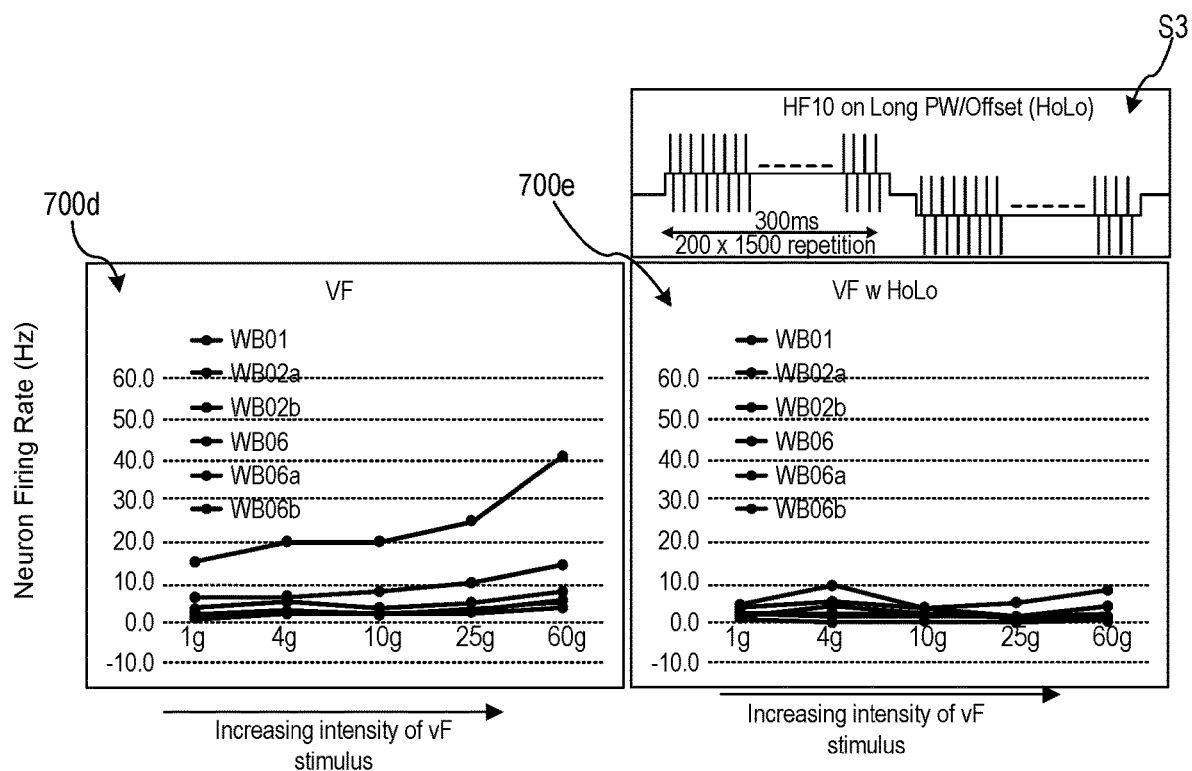

FIG. 7B depicts the neuron firing rate evoked in six different neurons of a second animal in response to the vF stimuli during application of the third signal and in the absence of any SCS signal. More specifically, FIG. 7B includes a fourth graph 700d illustrating the neuronal firing rate evoked by vF stimuli of various intensities in the absence of any SCS and a fifth graph 700e illustrating the neuronal firing rate evoked by vF stimuli of various intensities during application of the third signal (shown as S3 in FIG. 7B). The response in the fourth graph 700d is different than the response in the first graph 700a of FIG. 7A because the results shown in FIG. 7B were obtained using a different animal (and thus a different set of neurons) than the results shown in FIG. 7A. However, as with the graphs of FIG. 7A, the evoked neuronal responses shown in the graphs 700d and 700e are determined as the difference between the neuronal activity immediately following application of the vF stimulus and the neuronal activity immediately preceding application of the vF stimulus, with each line representing an individual neuron's response. As shown by the fourth graph 700d, in the absence of any SCS signal the evoked response to the vF stimuli generally increased as the intensity of the vF stimuli was increased. Of note, the fifth graph 700e shows a generally flatter evoked neural response (compared to the fourth graph 700d) as the vF stimuli was increased in intensity. Accordingly, the third signal S3 partially suppressed the neuronal firing evoked by the nociceptive vF stimulus (e.g., the third signal S3 at least partially suppressed the neurons) relative to the neuronal firing rate evoked in the absence of SCS.

Figure 7C:
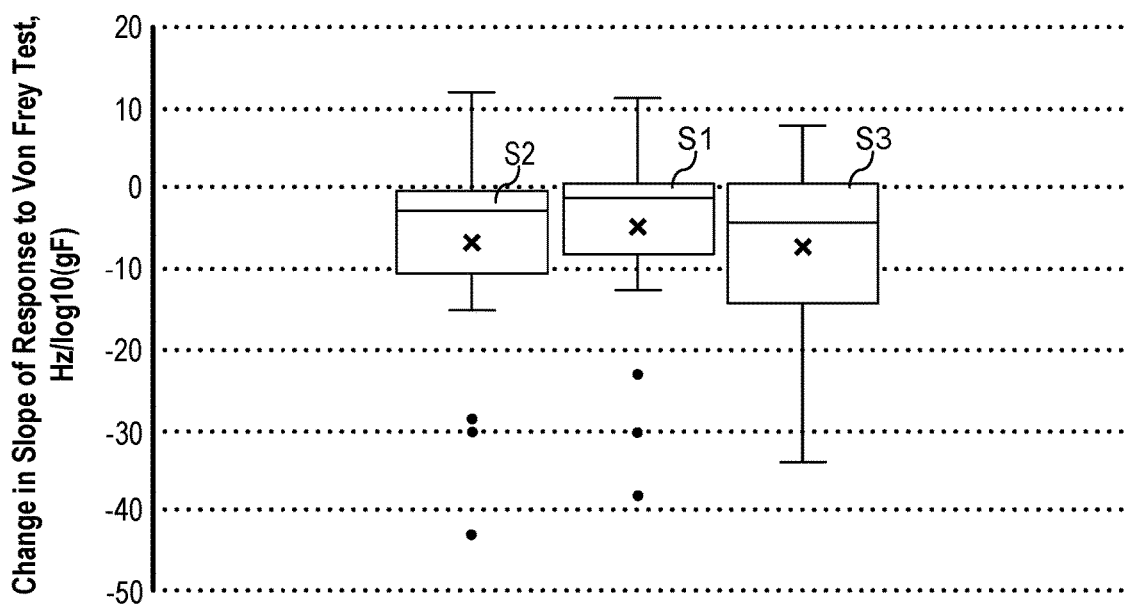

FIG. 7C is a graph showing the change in slope between the neural response evoked by the vF stimuli during application of SCS and the neural response evoked by the vF stimuli during periods of no SCS application. For the first signal S1, this includes the change in the average slope of the lines shown in graph 700b relative to the average slope of the lines shown in graph 700a of FIG. 7A. For the second signal S2, this includes the change in the average slope of the lines shown in the graph 700c relative to the average slope of the lines shown in the graph 700a of FIG. 7A. For the third signal S3, this includes the change in the average slope of the lines shown in graph 700e relative to the average slope of the lines shown in the graph 700d of FIG. 7B. In particular, a larger decrease in slope corresponds to a greater degree of neural suppression relative to the baseline.

As illustrated in FIGS. 7A-7C, the first therapy signal S1, the second therapy signal S2, and the third therapy signal S3 each significantly reduced the neuron firing evoked by the nociceptive vF stimulus. None of the therapy signals reduced neuron firing rate by a statistically significant amount relative to the other therapy signals, although the third signal S3 did tend to show, on average, a larger reduction in neuron firing than the first therapy signal S1 and the second therapy signal S2. Moreover, because these studies are preliminary, the reduction in firing rates achieved by administering the first signal S1 and the third signal S3, both of which have a relatively long pulse width in accordance with the present technology, is expected to increase as the amplitudes and other parameters for these signals are optimized. Also, due to the heterogeneity of nervous tissue and patient populations, the first signal S1 and/or the third signal S3 may produce a greater neural suppression for certain neurons and/or in certain patient populations.

6.0 Representative Examples

The following examples are provided to further illustrate embodiments of the present technology and are not to be interpreted as limiting the scope of the present technology. To the extent that certain embodiments or features thereof are mentioned, it is merely for purposes of illustration and, unless otherwise specified, is not intended to limit the present technology. It will be understood that many variations can be made in the procedures described herein while still remaining within the bounds of the present technology. Such variations are intended to be included within the scope of the presently disclosed technology.

1. A patient treatment system, comprising:
   a signal generator having a computer readable storage medium with instructions that, in operation, generate a therapy signal having a base component and a high frequency component, wherein—
   the base component has pulses with a non-zero amplitude and a pulse width in a pulse width range of from about 5 ms to about 2 seconds, and
   the high frequency component includes high frequency pulses having a frequency in a frequency range of from about 1.2 kHz and about 100 kHz, wherein the high frequency pulses have an origin at the non-zero amplitude of the base component; and
   a signal delivery element coupleable to the signal generator, wherein the signal delivery element is positionable proximate a spinal cord region, and, in operation, delivers the therapy signal to the spinal cord region.

2. The patient treatment system of example 1 wherein the pulse width of the base component pulses is in a pulse width range of from about 5 ms to about 100 ms.

3. The patient treatment system of examples 1 or 2 wherein the pulse width of the base component pulses is in a pulse width range of from about 50 ms to about 2 seconds.

4. The patient treatment system of any of examples 1-3 wherein the pulse width of the base component pulses is in a pulse width range of from about 100 ms to about 2 seconds.

5. The patient treatment system of any of examples 1-4 wherein the pulse width of the base component pulses is in a pulse width range of from about 500 ms to about 2 seconds.

6. The patient treatment system of any of examples 1-5 wherein the high frequency pulses have an amplitude greater than the non-zero amplitude of the base component pulses.

7. The patient treatment system of any of examples 1-6 wherein the high frequency pulses have a frequency of 10 kHz.

8. The patient treatment system of any of examples 1-7 wherein the high frequency pulses have a pulse width in a pulse width range of between about 10 microseconds and about 333 microseconds.

9. The patient treatment system of any of examples 1-8 wherein the high frequency pulses include bursts of high frequency pulses, wherein adjacent bursts of high frequency pulses are separated by a quiescent interval during which no high frequency pulses are delivered.

10. The patient treatment system of any of examples 1-9 wherein the base component pulses include a plurality of biphasic pulses having an anodic pulse phase and a cathodic pulse phase, and wherein at least one of the anodic pulse phase or the cathodic pulse phase has the pulse width in the pulse width range from about 5 ms to about 2 seconds.

11. The patient treatment system of example 10 wherein the high frequency pulses occur during the anodic pulse phase and/or the cathodic pulse phase.

12. The patient treatment system of examples 10 or 11 wherein the base component pulses include an interphase interval between the anodic pulse phase and the cathodic pulse phase, and wherein the high frequency pulses do not occur during the interphase interval.

13. The patient treatment system of any of examples 10-12 wherein adjacent bi-phasic pulses of the plurality of biphasic pulses of the base component pulses are separated by an interpulse interval, and wherein the high frequency pulses do not occur during the interpulse interval.

14. The patient treatment system of any of examples 10-13 wherein the high frequency pulses include bursts of high frequency pulses, wherein adjacent bursts of high frequency pulses are separated by a quiescent interval during which no high frequency pulses are delivered.

15. The patient treatment system of example 14 wherein at least two bursts of high frequency pulses occur during each anodic pulse phase and/or each cathodic pulse phase.

16. The patient treatment system of any of examples 1-9 wherein the base component pulses include a plurality of monophasic pulses having the non-zero amplitude.

17. The patient treatment system of any of examples 1-16 wherein the therapy signal at least partially suppresses at least a subset of neurons in the spinal cord region.

18. The patient treatment system of example 17 wherein the subset of neurons includes WDR neurons.

19. The patient treatment system of example 17 wherein the subset of neurons includes NS neurons.

20. The patient treatment system of example 17 wherein the subset of neurons includes both WDR neurons and NS neurons.

21. The patient treatment system of any of examples 1-20 wherein the signal delivery element includes an electrode, and wherein the non-zero amplitude of the base component pulses is selected to be at or below a maximum amplitude of the therapy signal that the electrode can tolerate based at least in part on the pulse width, the electrode material, and/or the surface area of the electrode.

22. A method for treating a patient, comprising:
programming a signal generator to deliver a therapy signal to a target neural population in the patient's spinal cord region via at least one implanted signal delivery element, wherein the therapy signal includes (i) a base component having pulses with a non-zero amplitude and a pulse width in a pulse width range of from about 5 ms to about 2 seconds, and (ii) a high frequency component including high frequency pulses having a frequency in a frequency range of from about 1.2 kHz and about 100 kHz, wherein the high frequency pulses have an origin at the non-zero amplitude of the base component.

23. The method of example 22 wherein the pulse width of the base component pulses is in a pulse width range of from about 5 ms to about 100 ms.

24. The method of examples 22 or 23 wherein the pulse width of the base component pulses is in a pulse width range of from about 50 ms to about 2 seconds.

25. The method of any of examples 22-24 wherein the pulse width of the base component pulses is in a pulse width range of from about 100 ms to about 2 seconds.

26. The method of any of examples 22-25 wherein the pulse width of the base component pulses is in a pulse width range of from about 500 ms to about 2 seconds.

27. The method of any of examples 22-26 wherein the high frequency pulses have an amplitude greater than the non-zero amplitude of the base component pulses.

28. The method of any of examples 22-27 wherein the high frequency pulses have a frequency of 10 kHz.

29. The method of any of examples 22-28 wherein the high frequency pulses have a pulse width in a pulse width range of between about 10 microseconds and about 333 microseconds.

30. The method of any of examples 22-29 wherein the high frequency pulses include bursts of high frequency pulses, wherein adjacent bursts of high frequency pulses are separated by a quiescent interval during which no high frequency pulses are delivered.

31. The method of any of examples 22-30 wherein the base component pulses include a plurality of biphasic pulses having an anodic pulse phase and a cathodic pulse phase, and wherein at least one of the anodic pulse phase or the cathodic pulse phase has the pulse width in the pulse width range from about 5 ms to about 2 seconds.

32. The method of example 31 wherein the high frequency pulses occur during the anodic pulse phase and/or the cathodic pulse phase.

33. The method of examples 31 or 32 wherein the base component pulses include an interphase interval between the anodic pulse phase and the cathodic pulse phase, and wherein the high frequency pulses do not occur during the interphase interval.

34. The method of any of examples 31-33 wherein adjacent bi-phasic pulses of the plurality of biphasic pulses of the base component pulses are separated by an interpulse interval, and wherein the high frequency pulses do not occur during the interpulse interval.

35. The method of any of examples 31-34 wherein the high frequency pulses include bursts of high frequency pulses, wherein adjacent bursts of high frequency pulses are separated by a quiescent interval during which no high frequency pulses are delivered.

36. The method of example 35 wherein at least two bursts of high frequency pulses occur during each anodic pulse phase and/or each cathodic pulse phase.

37. The method of any of examples 22-30 wherein the base component pulses include a plurality of monophasic pulses having the non-zero amplitude.

38. The method of any of examples 22-37 wherein the therapy signal at least partially suppresses at least a subset of neurons in the spinal cord region.

39. The method of example 38 wherein the subset of neurons includes WDR neurons.

40. The method of example 38 wherein the subset of neurons includes NS neurons.

41. The method of example 38 wherein the subset of neurons includes both WDR neurons and NS neurons.

42. The method of any of examples 22-41 wherein signal delivery element includes an electrode, and wherein the non-zero amplitude of the base component pulses is at or below a maximum amplitude of the therapy signal that the electrode can tolerate based at least in part on the pulse width, the electrode material, and/or the surface area of the electrode.

43. A method for treating a patient, comprising:
applying a therapy signal to the patient via a treatment system, wherein the treatment system includes a signal delivery element positioned proximate a spinal cord region of the patient, and wherein the therapy signal includes (i) a base component having pulses with a non-zero amplitude and a pulse width in a pulse width range of from about 5 ms to about 2 seconds, and (ii) a high frequency component including high frequency pulses having a frequency in a frequency range of from about 1.2 kHz and about 100 kHz, wherein the high frequency pulses have an origin at the non-zero amplitude of the base component.

44. The method of example 43 wherein the pulse width of the base component pulses is in a pulse width range of from about 5 ms to about 100 ms.

45. The method of examples 43 or 44 wherein the pulse width of the base component pulses is in a pulse width range of from about 50 ms to about 2 seconds.

46. The method of any of examples 43-45 wherein the pulse width of the base component pulses is in a pulse width range of from about 100 ms to about 2 seconds.

47. The method of any of examples 43-46 wherein the pulse width of the base component pulses is in a pulse width range of from about 500 ms to about 2 seconds.

48. The method of any of examples 43-47 wherein the high frequency pulses have an amplitude greater than the non-zero amplitude of the base component pulses.

49. The method of any of examples 43-48 wherein the high frequency pulses have a frequency of 10 kHz.

50. The method of any of examples 43-49 wherein the high frequency pulses have a pulse width in a pulse width range of between about 10 microseconds and about 333 microseconds.

51. The method of any of examples 43-50 wherein the high frequency pulses includes bursts of high frequency pulses, wherein adjacent bursts of high frequency pulses are separated by a quiescent interval during which no high frequency pulses are delivered.

52. The method of any of examples 43-51 wherein the base component pulses include a plurality of biphasic pulses having an anodic pulse phase and a cathodic pulse phase, and wherein at least one of the anodic pulse phase or the cathodic pulse phase has the pulse width in the pulse width range from about 5 ms to about 2 seconds.

53. The method of example 52 wherein the high frequency pulses occur during the anodic pulse phase and/or the cathodic pulse phase.

54. The method of examples 52 or 53 wherein the base component pulses include an interphase interval between the anodic pulse phase and the cathodic pulse phase, and wherein the high frequency pulses do not occur during the interphase interval.

55. The method of any of examples 52-54 wherein adjacent bi-phasic pulses of the plurality of biphasic pulses of the base component pulses are separated by an interpulse interval, and wherein the high frequency pulses do not occur during the interpulse interval.

56. The method of any of examples 52-55 wherein the high frequency pulses include bursts of high frequency pulses, wherein adjacent bursts of high frequency pulses are separated by a quiescent interval during which no high frequency pulses are delivered.

57. The method of example 56 wherein at least two bursts of high frequency pulses occur during each anodic pulse phase and/or each cathodic pulse phase.

58. The method of any of examples 43-51 wherein the base component pulses include a plurality of monophasic pulses having the non-zero amplitude.

59. The method of any of examples 43-58 wherein the therapy signal at least partially suppresses at least a subset of neurons in the spinal cord region.

60. The method of example 59 wherein the subset of neurons includes WDR neurons.

61. The method of example 59 wherein the subset of neurons includes NS neurons.

62. The method of example 59 wherein the subset of neurons includes both WDR neurons and NS neurons.

63. The method of any of examples 43-62 wherein the signal delivery element includes an electrode, and wherein the non-zero amplitude of the base component pulses is at or below a maximum amplitude of the therapy signal that the electrode can tolerate based at least in part on the pulse width, the electrode material, and/or the surface area of the electrode.

64. A method for determining a maximum amplitude for a therapy signal having a pulse width, the method comprising:
recording, at a plurality of incremental amplitudes, an electrode voltage potential for the therapy signal having the pulse width;
based on the recording, determining a distortion amplitude of the plurality of incremental amplitudes at which the therapy signal begins to distort; and
based at least in part on the distortion amplitude, determining the maximum amplitude for the therapy signal.

65. The method of example 64 wherein recording an electrode voltage potential for the therapy signal at the plurality of incremental amplitudes includes recording the trace of the electrode voltage potential at each of the plurality of incremental amplitudes.

66. The method of example 65 wherein determining a distortion amplitude includes analyzing a morphology of the electrode potential traces to identify a waveform distortion feature.

67. The method of any of examples 64-66, further comprising calculating a maximum charge density based at least in part on the set pulse width and the maximum amplitude.

68. The method of any of examples 64-67, further comprising programming a signal generator to deliver a therapy signal to a target neural population in a patient's spinal cord region, wherein the therapy signal has an amplitude less than or equal to the maximum amplitude.

7.0 Conclusion

From the foregoing, it will be appreciated that specific embodiments of the disclosed technology have been described herein for purposes of illustration, but that various modifications may be made without deviating from the technology. For example, therapy signals described herein can be delivered at combinations of parameter values within the foregoing ranges at values that are not expressly disclosed herein. Certain aspects of the technology described in the context of particular embodiments may be combined or eliminated in other embodiments. For example, the therapy signal can be monophasic with a passive charge elimination phase. In some embodiments, the foregoing techniques can be used to address patient deficits than pain. Further, while advantages associated with certain embodiments of the disclosed technology have been described in the context of those embodiments, other embodiments may also exhibit such advantages, and not all embodiments need necessarily exhibit such advantages to fall within the scope of the present technology. Accordingly, the disclosure and associated technology can encompass other embodiments not expressly shown or described herein.

The use of "and/or" in reference to a list of two or more items is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

Where a range of values is provided, it is understood that each intervening value, to the tenth of the unit of the lower limit unless the context clearly dictates otherwise, to between the upper and lower limits of that range is also specifically disclosed. Each smaller range between any stated value or intervening value in a stated range and any other stated or intervening value in that stated range is encompassed within the disclosure. The upper and lower limits of these smaller ranges may independently be included or excluded in the range, and each range where either, neither or both limits are included in the smaller ranges is also encompassed within the disclosure, subject to any specifically excluded limit in the stated range. Where the stated range includes one or both of the limits, ranges excluding either or both of those included limits are also included in the disclosure.

We claim:

1. A patient treatment system, comprising:
   a signal generator having a computer readable storage medium with instructions that, in operation, generate a therapy signal having a base component and a high frequency component, wherein—
   the base component has pulses with a non-zero amplitude and a pulse width in a pulse width range of from about 5 ms to about 2 seconds, and
   the high frequency component includes high frequency pulses having a frequency in a frequency range of from about 1.2 KHz to about 100 KHz, wherein the high frequency pulses have an origin at the non-zero amplitude of the base component; and
   a signal delivery element coupleable to the signal generator, wherein the signal delivery element is positionable proximate a spinal cord region, and, in operation, delivers the therapy signal to the spinal cord region.

2. The patient treatment system of claim 1 wherein the pulse width of the base component pulses is in a pulse width range of from about 5 ms to about 100 ms.

3. The patient treatment system of claim 1 wherein the pulse width of the base component pulses is in a pulse width range of from about 50 ms to about 2 seconds.

4. The patient treatment system of claim 1 wherein the pulse width of the base component pulses is in a pulse width range of from about 100 ms to about 2 seconds.

5. The patient treatment system of claim 1 wherein the pulse width of the base component pulses is in a pulse width range of from about 500 ms to about 2 seconds.

6. The patient treatment system of claim 1 wherein the high frequency pulses have an amplitude greater than the non-zero amplitude of the base component pulses.

7. The patient treatment system of claim 1 wherein the high frequency pulses have a frequency of 10 KHz.

8. The patient treatment system of claim 1 wherein the high frequency pulses have a pulse width in a pulse width range of between about 10 microseconds and about 333 microseconds.

9. A patient treatment system, comprising:
   a signal generator having a computer readable storage medium with instructions that, in operation, generate a therapy signal having a base component and a high frequency component, wherein—
   base component has pulses with a non-zero amplitude and a pulse width in a pulse width range of from about 5 ms to about 2 seconds, and
   the high frequency component includes bursts of high frequency pulses, wherein the high frequency pulses have a frequency in a frequency range of from about 1.2 kHz to about 100 kHz and an origin at the non-zero amplitude of the base component, and wherein adjacent bursts of high frequency pulses are separated by a quiescent interval during which no high frequency pulses are delivered; and
   a signal delivery element coupleable to the signal generator, wherein the signal delivery element is positionable proximate a spinal cord region, and, in operation, delivers the therapy signal to the spinal cord region.

10. The patient treatment system of claim 1 wherein the base component pulses include a plurality of biphasic pulses having an anodic pulse phase and a cathodic pulse phase, and wherein at least one of the anodic pulse phase or the cathodic pulse phase has the pulse width in the pulse width range from about 5 ms to about 2 seconds.

11. The patient treatment system of claim 10 wherein the high frequency pulses occur during the anodic pulse phase and/or the cathodic pulse phase.

12. The patient treatment system of claim 10 wherein the base component pulses include an interphase interval between the anodic pulse phase and the cathodic pulse phase, and wherein the high frequency pulses do not occur during the interphase interval.

13. The patient treatment system of claim 10 wherein adjacent bi-phasic pulses of the plurality of biphasic pulses of the base component pulses are separated by an interpulse interval, and wherein the high frequency pulses do not occur during the interpulse interval.

14. The patient treatment system of claim 10 wherein the high frequency pulses include bursts of high frequency pulses, wherein adjacent bursts of high frequency pulses are separated by a quiescent interval during which no high frequency pulses are delivered.

15. The patient treatment system of claim 14 wherein at least two bursts of high frequency pulses occur during each anodic pulse phase and/or each cathodic pulse phase.

16. The patient treatment system of claim 1 wherein the base component pulses include a plurality of monophasic pulses having the non-zero amplitude.

17. The patient treatment system of claim 1 wherein the therapy signal at least partially suppresses at least a subset of neurons in the spinal cord region.

18. The patient treatment system of claim 17 wherein the subset of neurons includes WDR neurons.

19. The patient treatment system of claim 17 wherein the subset of neurons includes NS neurons.

20. The patient treatment system of claim 17 wherein the subset of neurons includes both WDR neurons and NS neurons.

21. The patient treatment system of claim 1 wherein the signal delivery element includes an electrode, and wherein the non-zero amplitude of the base component pulses is selected to be at or below a maximum amplitude of the therapy signal that the electrode can tolerate based at least in part on the pulse width, the electrode material, and/or the surface area of the electrode.

22. A method for treating a patient, comprising:
programming a signal generator to deliver a therapy signal to a target neural population in the patient's spinal cord region via at least one implanted signal delivery element, wherein the therapy signal includes (i) a base component having pulses with a non-zero amplitude and a pulse width in a pulse width range of from about 5 ms to about 2 seconds, and (ii) a high frequency component including high frequency pulses having a frequency in a frequency range of from about 1.2 kHz to about 100 kHz, wherein the high frequency pulses have an origin at the non-zero amplitude of the base component.

23. A method for treating a patient, comprising:
applying a therapy signal to the patient via a treatment system, wherein the treatment system includes a signal delivery element positioned proximate a spinal cord region of the patient, and wherein the therapy signal includes (i) a base component having pulses with a non-zero amplitude and a pulse width in a pulse width range of from about 5 ms to about 2 seconds, and (ii) a high frequency component including high frequency pulses having a frequency in a frequency range of from about 1.2 KHz to about 100 kHz, wherein the high frequency pulses have an origin at the non-zero amplitude of the base component.

24. The method of claim 22 wherein the pulse width of the base component pulses is in a pulse width range of from about 500 ms to about 2 seconds.

25. The method of claim 22 wherein the high frequency pulses have an amplitude greater than the non-zero amplitude of the base component pulses.

26. The method of claim 22 wherein the high frequency pulses have a frequency of 10 KHz.

27. The method of claim 22 wherein the high frequency pulses have a pulse width in a pulse width range of between about 10 microseconds and about 333 microseconds.

28. The method of claim 22 wherein the base component pulses include a plurality of biphasic pulses having an anodic pulse phase and a cathodic pulse phase, and wherein at least one of the anodic pulse phase or the cathodic pulse phase has the pulse width in the pulse width range from about 5 ms to about 2 seconds.

29. The method of claim 28 wherein the base component pulses include an interphase interval between the anodic pulse phase and the cathodic pulse phase, and wherein the high frequency pulses do not occur during the interphase interval.

30. The method of claim 22 wherein the therapy signal at least partially suppresses at least a subset of neurons in the spinal cord region, and wherein the subset of neurons includes WDR neurons and/or NS neurons.

31. The method of claim 23 wherein the pulse width of the base component pulses is in a pulse width range of from about 100 ms to about 2 seconds.

32. The method of claim 23 wherein the high frequency pulses have a frequency of 10 KHz.

33. The method of claim 23 wherein the high frequency pulses have a pulse width in a pulse width range of between about 10 microseconds and about 333 microseconds.

* * * * *

UNITED STATES PATENT AND TRADEMARK OFFICE
CERTIFICATE OF CORRECTION

PATENT NO. : 12,133,981 B2
APPLICATION NO. : 17/837726
DATED : November 5, 2024
INVENTOR(S) : Dongchul Lee Page 1 of 1

It is certified that error appears in the above-identified patent and that said Letters Patent is hereby corrected as shown below:

On the Title Page

Item [56], in Column 2, under "Other Publications", Line 2, delete "Physcial" and insert -- Physical --.

On the page 2, item [56], in Column 2, under "Other Publications", Line 2, delete "refactory" and insert -- refractory --.

On the page 2, item [56], in Column 2, under "Other Publications", Line 11, delete "Neurotherapeautics," and insert -- Neurotherapeutics, --.

In the Drawings

On sheet 10 of 14, in FIG. 5A, reference numeral 508, Line 3, delete "electrode." and insert -- electrode --.

In the Claims

In Column 28, Line 22, in Claim 9, delete "base" and insert -- the base --.

Signed and Sealed this
Eighteenth Day of March, 2025

Coke Morgan Stewart
*Acting Director of the United States Patent and Trademark Office*